United States Patent
Frenz et al.

(10) Patent No.: US 10,988,808 B2
(45) Date of Patent: Apr. 27, 2021

(54) SYNTHESIZING BARCODING SEQUENCES UTILIZING PHASE-SHIFT BLOCKS AND USES THEREOF

(71) Applicant: Bio-Rad Laboratories, Inc., Hercules, CA (US)

(72) Inventors: Lucas Frenz, Oakland, CA (US); Jeremy Agresti, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 16/802,264

(22) Filed: Feb. 26, 2020

(65) Prior Publication Data

US 2020/0190579 A1 Jun. 18, 2020

Related U.S. Application Data

(63) Continuation of application No. 15/404,980, filed on Jan. 12, 2017, now Pat. No. 10,612,089.

(60) Provisional application No. 62/277,783, filed on Jan. 12, 2016.

(51) Int. Cl.
*C12Q 1/6874* (2018.01)
*C12Q 1/6806* (2018.01)

(52) U.S. Cl.
CPC ......... *C12Q 1/6874* (2013.01); *C12Q 1/6806* (2013.01)

(58) Field of Classification Search
CPC ............................ C12Q 1/6874; C12Q 1/6806
See application file for complete search history.

(56) References Cited

U.S. PATENT DOCUMENTS

2015/0005200 A1 1/2015 Hindson et al.
2015/0051088 A1 2/2015 Kim

OTHER PUBLICATIONS

Seringhaus, et al., "Mismatch oligonucleotides in human and yeast: guidelines for probe design on tiling microarrays", BMC Genomics, vol. 9, No. 635, 2008, pp. 1-14.
Wu, et al., "Phasing amplicon sequencing on Illumina Miseq for robust environmental microbial community analysis", BMC Microbiology., vol. 15, No. 125, 2015, pp. 1-12.
PCT/US2017/013205, "International Search Report and Written Opinion", dated May 18, 2017, 18 pages.
Extended European Search Report from EP Application 17738940.0 dated May 7, 2019; 8 pages.
Borgstrom E. et al.; "Phasing of single DNA molecules by massigvely parallel barcoding"; *Nature Communications*. vol. 6, No. 1; Jun. 9, 2015; 6 pgs.
Faircloth, B.C. et al.; "Not All Sequence Tags Are Created Equal: Designing and Validating Sequence Identification Tags Robust to Indels"; *PLOS ONE*. vol. 7, No. 8; Aug. 10, 2012; pp. e-42543; 11 pages.
Klein, A.M. et al.; "Droplet Barcoding for Single-Cell Transcriptomics Applied to Embryonic Stem Cells"; *Cell*. vol. 161, No. 5; May 1, 2015; pp. 1187-1201.
Parkinson, N.J. et al.; "Preparation of high-quality next-generation sequencing libraries from pictogram quantities of target DNA"; *Genome Research*. vol. 22, No. 1; Nov. 16, 2011; pp. 125-133.

*Primary Examiner* — Robert H Havlin
(74) *Attorney, Agent, or Firm* — Kilpatrick Townsend and Stockton LLP

(57) ABSTRACT

Provided herein are compositions and methods for generating phase-shift barcode oligonucleotides for library construction for next-generation sequencing. In some cases, barcode oligonucleotides are attached to particles or beads. Also provided are methods and kits for using the phase-shift barcode oligonucleotides in sequencing assays.

16 Claims, 4 Drawing Sheets

Specification includes a Sequence Listing.

SYNTHESIZING BARCODING SEQUENCES UTILIZING PHASE-SHIFT BLOCKS AND USES THEREOF

CROSS-REFERENCE TO RELATED PATENT APPLICATIONS

This application is a continuation of U.S. patent application Ser. No. 15/404,980, filed Jan. 12, 2017, which claims priority to U.S. Provisional Patent Application No. 62/277,783, filed Jan. 12, 2016, which is incorporated by reference herein in its entirety.

REFERENCE TO A SEQUENCE LISTING

The Sequence Listing written in file SequenceListing_094868-1178866-111120US.txt created on Feb. 24, 2020, 36,102 bytes, machine format IBM-PC, MS-Windows operating system, is hereby incorporated by reference in its entirety for all purposes.

BACKGROUND OF THE INVENTION

Next-generation sequencing can be used to assess the sequence of millions of DNA strands in parallel. For instance, in Illumina's sequencing technology, multiple clonal clusters of DNA are formed randomly on a surface, and sequencing by synthesizing is performed by using the cluster DNA as a substrate. During each sequencing cycle, one new base is evaluated on each of the DNA strands in parallel. Thus, it is important that the clusters be unambiguously identified during the synthesis steps. If all the clusters on a flowcell contain the same base at the same location, the software is unable to distinguish the base correctly and the sequencing quality can decrease, or the sequencing run can fail. Most sequencing platforms encounter this technical problem when a majority of the DNA strands to be sequenced have an identical base at the same position.

For some applications, it is desirable to label, tag, or barcode certain DNA molecules before sequencing. This means that the molecules to be sequences can contain at least two regions: (1) a barcode, and (2) capture nucleotides. It is typically necessary to have a large number of different barcodes as well as have identical copies of these barcodes. It is desirable to label DNA molecules that are meant to be grouped together with the same barcode. Identical barcodes can either be included in different wells or tubes, or in other cases, they can be physically linked to a plurality of beads.

There are a number of different ways to create the barcode and capture nucleotides. For instance, primer extension can be used for synthesis. By employing this method, the barcode nucleotides can have at least two regions: (1) nucleotides used as a barcode, and (2) nucleotides used as either priming, hybridization, or linking sites. As such, the entire barcoding region can be synthesized using building blocks by piecing the blocks together by, e.g., ligation, hybridization or PCR utilizing constant, universal priming sites. These constant, universal priming sites can cause sequencing problems. For example, the majority of the sequences can have identical or nearly identical nucleotide patterns (sequences) at the same positions along the DNA strands. In some cases, the sequences may have low diversity at every position.

Solutions to this problem include using random, non-relevant sequences such as a PhiX control (Illumina) in the sequencing run to increase diversity across the clusters. This creates sufficient variation during each sequencing cycle, but dilutes the accurate samples and reduces the sequencing capacity.

BRIEF SUMMARY OF THE INVENTION

In one aspect, provided herein is a library of barcode oligonucleotides, each barcode oligonucleotide comprising a variable region (e.g., a barcode region), a universal region (e.g., a defined region), and a phase-shift region, wherein a first nucleotide of the defined region of a first barcode oligonucleotide is staggered by 1 to 50 nucleotides from the first nucleotide of the defined region of a second barcode oligonucleotide.

The barcode oligonucleotides can be free in solution or attached to beads. The barcode oligonucleotides can be in partitions such as wells, tubes, or plates. In some embodiments, one or more barcode oligo nucleotides are in a partition. In some cases, different barcode oligonucleotides are found in different partitions, e.g., different wells or different tubes. In some embodiments, each barcode oligonucleotide is in a separate partition. In other embodiments, each barcode oligonucleotide is attached to a bead. The bead can be a hydrogel bead, plastic bead, glass bead or metal bead.

In some embodiments, the phase-shift region is before (e.g., 5' to) the universal region. In some embodiments, the phase-shift region of each of the plurality of barcode oligonucleotides is substantially unique and 1-50 nucleotides in length.

In some instances, the universal region is linked to a nucleotide sequence at its 3' end.

The variable region of each of the plurality of barcode oligonucleotides can be substantially unique and at least 3 nucleotides in length. In some cases, each barcode oligonucleotide comprises more than one variable region. The universal region of each of the plurality of barcode oligonucleotides can be substantially identical and at least 6 nucleotides in length. In other cases, each barcode oligonucleotide comprises more than one universal region.

Each barcode oligonucleotide of the library can also include a capture region. In some cases, the capture region comprises a poly-thymine sequence, poly-adenosine sequence, or a random sequence.

In another aspect, provided herein is a library of barcode beads (e.g., particles) comprising a plurality of beads conjugated to a plurality of barcode oligonucleotides wherein each bead is conjugated to a different barcode oligonucleotide. Each barcode oligonucleotide comprises: a variable region (e.g., a barcode region), a universal region (e.g., a defined region), and a phase-shift region, wherein a first nucleotide of the universal region of a first barcode oligonucleotide is staggered by 1 to 50 nucleotides from the first nucleotide of the universal region of a second barcode oligonucleotide, and wherein each bead is conjugated to at least two of the same barcode oligonucleotides. Each barcode oligonucleotide can also include a capture region (capture sequence).

In some embodiments, the phase-shift region is located before the universal region. In some instances, within and after the universal region there are at least two different nucleotides at any position of the barcode oligonucleotides in the plurality of barcode oligonucleotides.

In some embodiments, the universal region is identical in the plurality of barcode oligonucleotides. The phase-shift region of each of the plurality of barcode oligonucleotides can be substantially unique and 1-50 nucleotides in length.

The variable region of each of the plurality of barcode oligonucleotides can be substantially unique and at least 3 nucleotides in length. The universal region of the plurality of barcode oligonucleotides can be identical and at least 6 nucleotides in length.

In some embodiments, each barcode oligonucleotide comprises more than one variable region. Each barcode oligonucleotide can comprise more than one universal region.

In some instances, each barcode oligonucleotide further comprises a unique molecular identifier. The unique molecular identifier can comprise 3-100 nucleotides. In some embodiments, each barcode oligonucleotide further comprises a capture region.

In some embodiments, each bead is conjugated to at least two different barcode oligonucleotides. The bead can be a hydrogel bead, a plastic bead such as a polystyrene bead or a PMMA bead, a glass bead, or a metal bead.

In another aspect, provided herein is a kit comprising any one of the libraries of barcode oligonucleotides disclosed herein or any one of the libraries of barcode oligonucleotide beads disclosed herein, and a reagent for partitioning the library into a plurality of partitions. The reagent for partitioning can comprise a water immiscible liquid.

In yet another aspect, provided herein is a method for analyzing nucleic acid of a population of cells. The method includes providing any one of the libraries of barcode oligonucleotides disclosed herein or any one of the libraries of barcode oligonucleotide beads disclosed herein; providing a population of cells; partitioning the library of barcode oligonucleotides or the library of barcode oligonucleotide beads and the population of cells to generate a plurality of partitions (e.g., wells, tubes, plates or droplets) having a single barcode oligonucleotide and nucleic acid from a single cell; lysing the population of cells to generate nucleic acid from a single cell; hybridizing the barcode oligonucleotide to the nucleic acid from the single cell in each partition; performing template directed nucleic acid polymerization to covalently attach oligonucleotide primers to the nucleic acid of the single cell in each partition; and performing high-throughput sequencing.

In some embodiments, the nucleic acid of the single cell is RNA or cDNA.

In some embodiments, the template directed nucleic acid polymerization comprises reverse transcription. The template directed nucleic acid polymerization can include DNA amplification.

In another aspect, provided herein is a method of synthesizing any one of the libraries of barcode oligonucleotides disclosed herein. The method includes: (a) annealing a primer to a nucleotide sequence, wherein the primer comprises a sequence complementary to a portion of the nucleotide sequence, the variable region, the universal region, and the phase-shift region; (b) extending the annealed primer to form a bead attached to the barcode oligonucleotide comprising the variable region, the universal region, and the phase-shift region; (c) displacing the annealed first primer; and repeating steps (a) to (c) to generate a library of barcode oligonucleotides.

In some embodiments, the method further comprises performing a primer extension to add one or more variable regions and/or one or more universal regions to each barcode oligonucleotide. In some instances, the method includes performing primer extension to add a capture region to each barcode oligonucleotide. In some embodiments, the capture region can comprise a poly-thymine sequence, poly-adenosine sequence, or a random sequence.

The method can also include attaching the nucleotide sequence of step (a) to a bead, thereby generating a library of barcode oligonucleotide beads.

In yet another aspect, libraries of phase-shift barcode oligonucleotides and libraries of phase-shift barcode oligonucleotides attached to a solid support (e.g., a bead) are provided. In some embodiments, the phase-shift barcode oligonucleotide comprises a phase-shift region having a length of 1-50 nucleotides, one or more variable regions (e.g., a barcode region), and one or more universal regions (e.g., a defined region). In some embodiments, the first nucleotide of the universal region (e.g., defined region) of a first barcode oligonucleotide in the library is staggered by 1 to 50 nucleotides from the first nucleotide of the universal region (e.g., defined region) of a second barcode oligonucleotide in the library when the first barcode oligonucleotide and the second barcode oligonucleotide are aligned.

In some embodiments, the phase-shift region is before (is 5' to) the universal region. In some embodiments, the phase-shift region has a length of 1 to 50 nucleotides. In some embodiments, the phase-shift region of a barcode oligonucleotide is about 2-40 nucleotides in length, about 2-20 nucleotides in length, about 2-10 nucleotides in length, about 5-50 nucleotides in length, about 10-50 nucleotides in length, about 5-30 nucleotides in length, about 5-10 nucleotides in length, or about 10-30 nucleotides in length. In some embodiments, the phase-shift region of a barcode oligonucleotide is 1, 2, 3, 4, 5, 6, 7, 8, 9, 10, 15, 20, 25, 30, 35, 40, 45, or 50 nucleotides in length. In some embodiments, the phase-shift region is at least 5 nucleotides in length. In some embodiments, the phase-shift region is at least 10 nucleotides in length. In some embodiments, the barcode oligonucleotides comprise one of at least 2, 3, 4, 5, 6, 7, 8, 9, 10, 20, 30, 40, 50, 60, 70, 80, 90, 100 or more unique phase-shift regions.

In some embodiments, the variable region of each of the plurality of phase-shift barcode oligonucleotides is at least 3 nucleotides in length, e.g., at least 5 nucleotides in length, at least 6 nucleotides in length, at least 9 nucleotides in length, at least 12 nucleotides in length, or at least 15 nucleotides in length. In some embodiments, the variable region is about 3-20 nucleotides in length, about 5-15 nucleotides in length, about 6-20 nucleotides in length, about 6-15 nucleotides in length, or about 5-10 nucleotides in length. In some embodiments, each barcode oligonucleotide comprises more than one variable region (e.g., 2, 3, 4, 5, 6, 7, 8, 9, 10 or more variable regions). In some embodiments, the barcode oligonucleotides comprise one of at least 5, 10, 15, 20, 30, 40, 50, 60, 70, 80, 90, 100, 250, 500, 1000, 2500, 5000, 7500, 10,000, 50,000, 100,000 or more unique variable regions or unique combinations of variable regions.

In some embodiments, the universal region of each of the plurality of phase-shift barcode oligonucleotides is at least 6 nucleotides in length, e.g., at least 10 nucleotides in length, at least 15 nucleotides in length, at least 20 nucleotides in length, at least 30 nucleotides in length, at least 40 nucleotides in length, or at least 50 nucleotides in length. In some embodiments, the universal region is about 6-100 nucleotides in length, about 6-75 nucleotides in length, about 6-50 nucleotides in length, about 6-20 nucleotides in length, about 10-50 nucleotides in length, about 10-30 nucleotides in length, or about 6-15 nucleotides in length. In some embodiments, each barcode oligonucleotide comprises more than one universal region (e.g., 2, 3, 4, 5, 6, 7, 8, 9, 10 or more universal regions).

In some cases, each barcode oligonucleotide of the library comprises more than one variable region. In some embodiments, each barcode oligonucleotide comprises two, three, four, or more variable regions. In some embodiments, wherein each barcode oligonucleotide comprises two, three, four, or more variable regions, the variable regions are separated by one or more universal regions. In some embodiments, wherein each barcode oligonucleotide comprises two, three, four, or more variable regions, each variable region is selected from a group of at least 5, 10, 15, 20, 30, 40, 50, 60, 70, 80, 90, 100 or more unique variable regions. In some embodiments, wherein each barcode oligonucleotide comprises two, three, four, or more variable regions, the variable regions are separated by one or more universal regions. In some embodiments, one or more of the universal regions are identical for all or most of the barcode oligonucleotides in the library.

In some embodiments, the phase-shift barcode oligonucleotides further comprise a capture region. In some embodiments, the capture region comprises a poly-thymine sequence, poly-adenosine sequence, or a random sequence (e.g., a randomer). In some embodiments, the capture region has a length of about 5-50 nucleotides, about 10-50 nucleotides, about 10-40 nucleotides, about 10-25 nucleotides, about 15-50 nucleotides, about 15-30 nucleotides, or about 20-50 nucleotides. In some embodiments, the capture region is at the 3' end of the barcode oligonucleotide.

In some embodiments, the phase-shift barcode oligonucleotides are free in solution. In some embodiments, the phase-shift barcode oligonucleotides are in partitions such as droplets, wells, tubes, or plates. In some embodiments, one or more phase-shift barcode oligonucleotides are in a partition. In some embodiments, each partition has an average of 0.1, 0.5, 1, 2, 3, 4, 5, 6, 7, 8, 9, 10, 20, 30, 40, 50 or more phase-shift barcode oligonucleotides. In some cases, different barcode oligonucleotides are found in different partitions, e.g., different droplets, different wells or different tubes. In some embodiments, each barcode oligonucleotide is in a separate partition.

In some embodiments, the phase-shift barcode oligonucleotides are attached to a solid support (e.g., particles or beads). In some embodiments, the bead is a hydrogel bead, plastic bead such as a polystyrene bead or a poly(methyl methacrylate) (PMMA) bead, glass bead or metal bead.

In some embodiments, the library of phase-shift barcode oligonucleotides or the library of phase-shift barcode oligonucleotides attached to a solid support (e.g., a particle or bead) comprises at least 100; 200; 300; 500; 750; 1000; 2500; 5000; 7500; 10,000; 15,000; 20,000; 30,000; 50,000; 75,000; 100,000; 250,000; 500,000; 1,000,000 or more unique barcode oligonucleotides. In some embodiments, each particle of the library is conjugated to one or more copies of a unique phase-shift barcode oligonucleotide. In some embodiments, each bead is conjugated to at least two copies (e.g., 2, 5, 10, 50, 100, 500, 1000, 5000, 10,000 or more copies) of the same phase-shift barcode oligonucleotide.

In still another aspect, provided herein are kits comprising any one of the libraries of phase-shift barcode oligonucleotides disclosed herein or any one of the libraries of phase-shift barcode oligonucleotide attached to a particle or bead as disclosed herein. In some embodiments, the kit further comprises a reagent for partitioning the library into a plurality of partitions. In some embodiments, the reagent for partitioning comprises a water immiscible liquid.

In yet another aspect, methods for analyzing a nucleic acid sample are provided. In some embodiments, the method comprises providing any one of the libraries of barcode oligonucleotides disclosed herein or any one of the libraries of barcode oligonucleotide beads disclosed herein; providing a nucleic acid sample; partitioning the library of barcode oligonucleotides or the library of barcode oligonucleotide beads and the nucleic acid sample to generate a plurality of partitions (e.g., wells, tubes, plates or droplets) having a single barcode oligonucleotide and nucleic acid; hybridizing the barcode oligonucleotide to the nucleic acid in each partition; performing template directed nucleic acid polymerization to covalently attach oligonucleotide primers to the nucleic acid in each partition; and performing high-throughput sequencing.

In some embodiments, the nucleic acid sample comprises a population of cells. In some embodiments, the nucleic acid (e.g., nucleic acid of the single cell) is RNA or cDNA.

In some embodiments, the template directed nucleic acid polymerization comprises reverse transcription. In some embodiments, the template directed nucleic acid polymerization comprises DNA amplification.

In another aspect, methods of synthesizing a library of phase-shift barcode oligonucleotides are provided. In some embodiments, the method comprises:

(a) providing a plurality of primer oligonucleotides and at least a first template oligonucleotide and a second template oligonucleotide, wherein each of the first template oligonucleotide and the second template oligonucleotide comprises a universal region, a variable region, and a phase-shift region and further comprises a sequence that is complementary to a portion of the primer oligonucleotide sequence and wherein the phase-shift region of the first template oligonucleotide has a different length than the length of the phase-shift region of the second template oligonucleotide;

(b) annealing the template oligonucleotides to the primer oligonucleotides;

(c) extending the primer oligonucleotides having annealed template oligonucleotides to form barcode oligonucleotides comprising the phase-shift region, the variable region, and the universal region; and (d) displacing the annealed template oligonucleotides.

In some embodiments, the template oligonucleotide comprises a phase-shift region as described herein, e.g., a phase-shift region having a length of 1 to 50 nucleotides, e.g., about 2-40 nucleotides in length, about 2-20 nucleotides in length, about 2-10 nucleotides in length, about 5-50 nucleotides in length, about 10-50 nucleotides in length, about 5-30 nucleotides in length, about 5-10 nucleotides in length, or about 10-30 nucleotides in length. In some embodiments, the template oligonucleotide comprises a phase-shift region that is at least 5 nucleotides in length or at least 10 nucleotides in length. In some embodiments, the template oligonucleotide comprises a variable region as described herein, e.g., a variable region that is at least 3 nucleotides in length, e.g., at least 5, 6, 9, 12, or 15 nucleotides in length. In some embodiments, the template oligonucleotide comprises a variable region that is about 3-20 nucleotides in length, about 5-15 nucleotides in length, about 6-20 nucleotides in length, about 6-15 nucleotides in length, or about 5-10 nucleotides in length. In some embodiments, the template oligonucleotide comprises a universal region as described herein, e.g., a universal region that is at least 6 nucleotides in length, e.g., at least 10, 15, 20, 30, 40, or 50 nucleotides in length. In some embodiments, the template oligonucleotide comprises a universal region that is about 6-100 nucleotides in length, about 6-75 nucleotides in length, about 6-50 nucleotides in length, about 6-20 nucleotides in length, about 10-50 nucleotides in length, about 10-30 nucleotides in length, or about 6-15 nucleotides in length.

In some embodiments, the method comprises providing at least 2, 3, 4, 5, 6, 7, 8, 9, 10, 15, 20, 25, 30, 40, 50, 60, 70, 80, 90, 100 or more template oligonucleotides. In some embodiments, the template oligonucleotides comprise one of at least 2, 3, 4, 5, 6, 7, 8, 9, 10, 20, 30, 40, 50, 60, 70, 80, 90, 100 or more unique phase-shift regions and one of at least 5, 10, 15, 20, 30, 40, 50, 60, 70, 80, 90, 100, 250, 500, 1000 or more unique variable regions. In some embodiments, each of the template oligonucleotides comprises a unique phase-shift region and a unique variable region. In some embodiments, each of the template oligonucleotides or most of the template oligonucleotides comprise an identical universal region.

In some embodiments, the method comprises providing at least 2, 3, 4, 5, 6, 7, 8, 9, 10, 15, 20, 25, 30, 40, 50, 60, 70, 80, 90, 100, 500, 1000, 5000, 10,000 or more primer oligonucleotides. In some embodiments, the plurality of primer oligonucleotides have identical sequences.

In some embodiments, the method further comprises performing a primer extension using a template oligonucleotide comprising a universal region, a variable region, and a sequence that is complementary to a portion of the barcode oligonucleotide sequence to add one or more further variable regions and/or one or more further universal regions to each barcode oligonucleotide. In some embodiments, the method comprises repeating steps (b) to (d) using a template oligonucleotide comprising a universal region, a variable region, and a sequence that is complementary to a portion of the barcode oligonucleotide sequence. In some embodiments, the further primer extension is performed using a plurality of template oligonucleotides (e.g., at least 2, 3, 4, 5, 6, 7, 8, 9, 10, 20, 30, 40, 50, 60, 70, 80, 90, 100 or more template oligonucleotides). In some embodiments, the template oligonucleotides comprise one of at least 5, 10, 15, 20, 30, 40, 50, 60, 70, 80, 90, 100, 250, 500, 1000 or more unique variable regions. In some embodiments, each of the template oligonucleotides comprises a unique variable region. In some embodiments, each of the template oligonucleotides or most of the template oligonucleotides comprise an identical universal region.

In some embodiments, steps (b) to (d) can be repeated 1, 2, 3, 4, 5, 6, 7, 8, 9, 10 or more times to add further variable regions and/or further universal regions to each barcode oligonucleotide.

In some embodiments, the method further comprises performing a primer extension using a template oligonucleotide comprising a capture region and a sequence that is complementary to a portion of the barcode oligonucleotide sequence to add a capture region to each barcode oligonucleotide. In some instances, the method further comprises performing primer extension using one or more template oligonucleotides (e.g., 1, 2, 3, 4, 5, 6, 7, 8, 9, 10, 20, 30, 40, 50, 60, 70, 80, 90, 100 or more template oligonucleotides) comprising a unique molecular identifier and a sequence that is complementary to a portion of the barcode oligonucleotide sequence to add a unique molecular identifier to each barcode oligonucleotide.

In some embodiments, each of the primer oligonucleotides of step (a) are attached to a bead. Thus, in some embodiments, the method comprises synthesizing a library of beads attached to barcode oligonucleotides.

Other objects, features, and advantages of the present invention will be apparent to one of skill in the art from the following detailed description and figures.

BRIEF DESCRIPTION OF THE DRAWINGS

FIG. 2 shows an exemplary embodiment of a barcode synthesis method using combinations of barcode building blocks with phase-shift sequences inserted after a barcode building block and before a universal region (SEQ ID NOs: 88-116, where BC building blocks are 6 nucleotides long).

FIG. 4 provides an exemplary method for building phase-shift barcode oligonucleotides (SEQ ID NOS: 11-22, 117 and 118) on beads.

DETAILED DESCRIPTION OF THE INVENTION

I. Introduction

Figure 1:
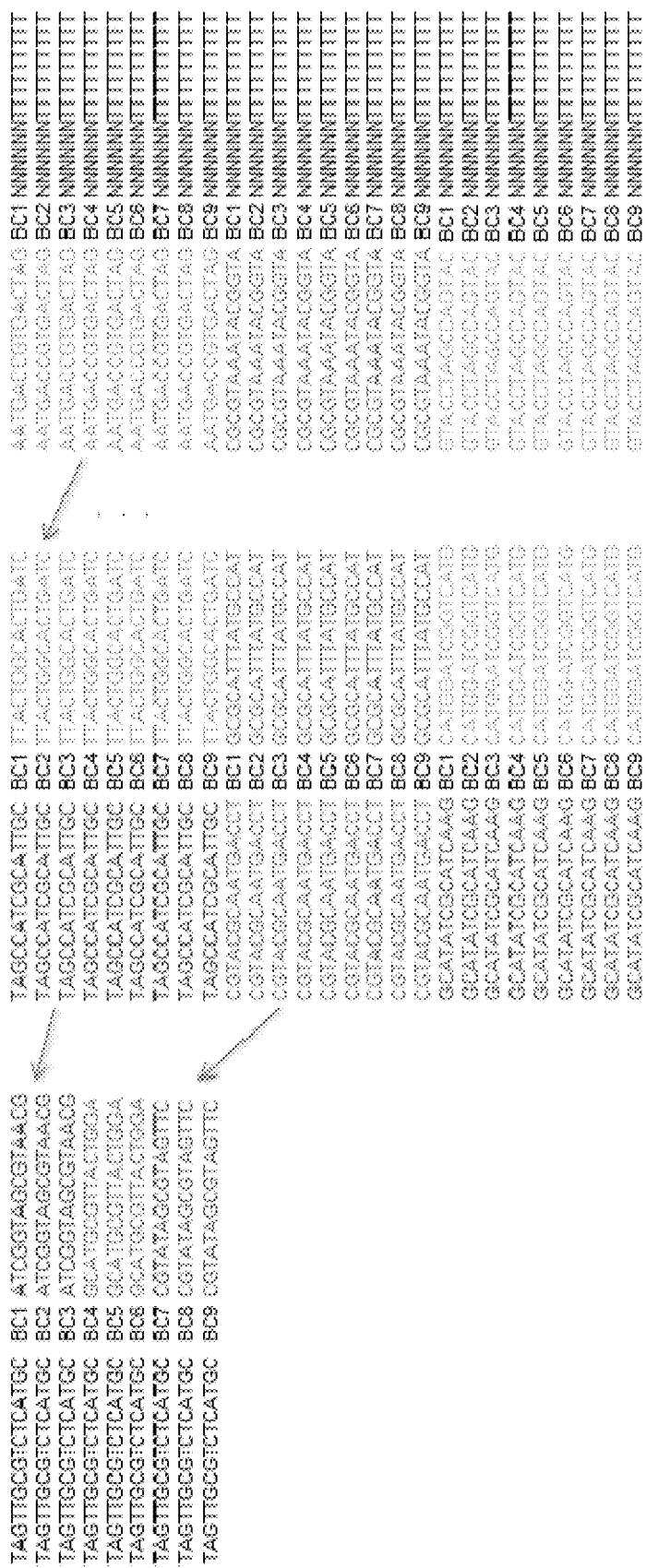
FIG. 1 shows an exemplary embodiment of a barcode synthesis method using combinations of barcode ("BC") building blocks without phase-shift sequences (SEQ ID NOs: 23-87, where BC building blocks are 6 nucleotides long).

Provided herein are compositions, methods and kits for generating a plurality of unique barcode sequences that are useful for synthesizing a nucleic acid library for next-generation sequencing such that nucleic acids of the library do not have identical nucleotides at the same position. When sequencing multiple nucleic acids (DNA strands) in parallel, the presence of the same base at the same position for a majority of the reads results in inaccurate base calling, diminished sequence quality, and/or sequencing run failures. The barcode sequences disclosed herein each include a phase-shift region that prevents all of the DNA strands from having an identical nucleotide at the same position when the barcode sequences are aligned. As such, the compositions and methods of the present invention create sufficient diversity in regions of the nucleic acid to be sequenced that otherwise have low diversity or identical sequences. The present methods and composition are useful for the preparation of a sequencing library.

The compositions, methods, and kits disclosed herein involve synthesizing (producing or generating) barcode oligonucleotide-containing particles or beads by performing primer extension reactions. The barcode oligonucleotide-containing particles can be used to capture nucleic acid, e.g., RNA from cells, and synthesize barcoded nucleic acid, e.g., cDNA.

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a bead" includes a plurality of such beads and reference to "the sequence" includes reference to one or more sequences known to those skilled in the art, and so forth.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2nd ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "barcode" refers to a short nucleotide sequence (e.g., at least about 2, 3, 4, 6, 8, 10, or 12, nucleotides long) that identifies a molecule to which it is conjugated. Barcodes can be used, e.g., to identify molecules in a partition (e.g., well, tube, plate or droplet). Such a partition-specific barcode should be unique for that partition as compared to barcodes present in other partitions. For example, partitions containing target RNA from single cells can be subject to reverse transcription conditions using primers that contain a different partition-specific barcode sequence in each partition, thus incorporating a copy of a unique "cellular barcode" into the reverse transcribed nucleic acids of each partition. Thus, nucleic acid from each cell can be distinguished from nucleic acid of other cells due to the unique "cellular barcode." In some cases, the cellular barcode is provided by a "particle barcode" that is present on oligonucleotides conjugated to a particle, wherein the particle barcode is shared by (e.g., identical or substantially identical amongst) all, or substantially all (e.g., among the majority, or among at least 80%, at least 90%, at least 95%, at least 96%, at least 97%, at least 98%, or at least 99%), of the oligonucleotides conjugated to that particle. Thus, cellular and particle barcodes can be present in a partition, attached to a particle, or bound to cellular nucleic acid as multiple copies of the same barcode sequence. Cellular or particle barcodes of the same sequence can be identified as deriving from the same cell, partition, or particle. Such partition-specific, cellular-specific, or particle-specific barcodes can be generated using a variety of methods, which methods result in the barcode conjugated to or incorporated into a solid or hydrogel support (e.g., a solid bead or particle or hydrogel bead or particle). In some cases, the partition-specific, cellular-specific, or particle-specific barcode is generated using a split and mix (also referred to as split and pool) synthetic scheme as described herein. A partition-specific barcode can be a cellular barcode and/or a particle barcode. Similarly, a cellular barcode can be a partition specific barcode and/or a particle barcode. Additionally, a particle barcode can be a cellular barcode and/or a partition-specific barcode.

In other cases, barcodes uniquely identify the molecule to which it is conjugated. For example, by performing reverse transcription using primers that each contain a unique "molecular barcode." In still other examples, primers can be utilized that contain "partition-specific barcodes" unique to each partition, and "molecular barcodes" unique to each molecule. After barcoding, partitions can then be combined, and optionally amplified, while maintaining virtual partitioning. Thus, e.g., the presence or absence of a target nucleic acid (e.g., reverse transcribed nucleic acid) comprising each barcode can be counted (e.g. by sequencing) without the necessity of maintaining physical partitions.

The length of the barcode sequence determines how many unique samples can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N-1 deletions or other mutations from the canonical barcode sequence. Thus, barcodes that are referred to as "identical or substantially identical copies" refer to barcodes that differ due to one or more errors in, e.g., synthesis, polymerization, or purification and thus contain various N-1 deletions or other mutations from the canonical barcode sequence. Moreover, the random conjugation of barcode nucleotides during synthesis using e.g., a split and pool approach and/or an equal mixture of nucleotide precursor molecules as described herein, can lead to low probability events in which a barcode is not absolutely unique (e.g., different from other barcodes of a population or different from barcodes of a different partition, cell, or bead). However, such minor variations from theoretically ideal barcodes do not interfere with the single cell analysis methods, compositions, and kits described herein. Therefore, as used herein, the term "unique" in the context of a particle, cellular, partition-specific, or molecular barcode encompasses various inadvertent N-1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Katsuyuki Shiroguchi, et al. Proc Natl Acad Sci USA., 2012 Jan. 24; 109(4):1347-52; and Smith, A M et al., Nucleic Acids Research (2010), 38(13):e142.

The term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel, well, tube, and plate. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

The term "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., PCR Protocols: A Guide to Methods and Applications, Innis et al., eds, 1990. Primers can be DNA, RNA, or a chimera of DNA and RNA portions. In some cases, primers can include one or more modified or non-natural nucleotide bases. In some cases, primers are labeled.

The term "target nucleic acid" refers to a polynucleotide such as DNA, e.g., single stranded DNA or double stranded DNA, RNA, e.g., mRNA or miRNA, or a DNA-RNA hybrid. DNA includes genomic DNA and complementary DNA (cDNA).

The term "template nucleic acid" refers to a polynucleotide template that is used to generate a second polynucleotide strand that can be complementary to the template or a portion thereof. In some embodiments, in a reverse transcription reaction an RNA template is used to generate a DNA that is complementary to the RNA. In other embodiments, a first strand cDNA is used as a template during polymerase based amplification to generate a second stand cDNA that is complementary to the first strand.

As used herein, the following terms have the meanings ascribed to them unless specified otherwise.

III. Detailed Description of Embodiments

A. Phase-Shift Barcode Oligonucleotides and Particle-Conjugated Phase-Shift Barcode Oligonucleotides Provided herein are barcode oligonucleotide sequences comprising a phase-shift region ("phase-shift barcode oligonucleotides"). As detailed herein, in a library of phase-shift barcode oligonucleotides, the presence of a phase-shift region of variable length in each of the sequences results in the barcode oligonucleotide sequences having staggered or shifted start positions for the universal region, when multiple barcode oligonucleotide sequences are aligned. This results in a diversity of bases at a given position in the universal region, which is advantageous when analyzing the sequences, such as by sequencing applications. In some embodiments, a phase-shift barcode oligonucleotide is a single-stranded oligonucleotide that is useful for hybridizing to a target nucleic acid. In some embodiments, the target nucleic acid is DNA (e.g., genomic DNA or long fragment DNA), RNA (mRNA, lncRNA, etc.), or a DNA/RNA hybrid.

Sequencing library preparation methods can include performing reverse transcription of nucleic acid (e.g., RNA) from a biological sample and attaching unique barcode sequences to nucleic acid of the sequencing library (e.g., cDNA). Such methods can include using particle- or bead-synthesized barcode oligonucleotides. Barcode beads can contain one or more barcodes such as a bead-specific barcode, a molecular barcode, a partition-specific barcode, and the like.

In some embodiments, the barcode oligonucleotides are conjugated to particles (e.g., beads). In some embodiments, a particle or bead comprises a solid support surface, the solid support surface having a plurality of oligonucleotides. For instance, a solid support surface can be conjugated to hundreds, thousands, or millions of oligonucleotides. In some embodiments, all or substantially all (e.g., the majority, or at least 80%, at least 90%, at least 95%, at least 96%, at least 97%, at least 98%, or at least 99% of) such phase-shift barcode oligonucleotides on a particle are identical. In other embodiments, at least two phase-shift barcode oligonucleotides on a particle are different.

Optionally, the phase-shift barcode oligonucleotides are not conjugated to particles. The phase-shift barcode sequences can be free in solution and found in partitions such as wells, tubes, plates, microchannels, droplets, and the like. In some embodiments, different barcode sequences are in different partitions. In some cases, at least two barcode oligonucleotides having the same sequence are in the same partition. In one embodiment of the method for using the barcode sequences, the barcode oligonucleotides are synthesized in a partition and a target nucleic acid of interest (e.g., an RNA of interest) can be captured in the partition.

1. Barcode Oligonucleotides

The phase-shift barcode oligonucleotide sequences comprise one or more variable regions (e.g., a barcode region), one or more universal regions (e.g., a defined region), and a phase-shift region of one or more nucleotides (e.g., 1-50 nucleotides) that is 5' to the universal region. In some embodiments, the phase-shift region is 5' to the one or more universal regions and is 5' to the one or more variable regions. In some embodiments, the phase-shift regions of the barcode oligonucleotide sequences within a library are of variable length and nucleotide composition, such that the library comprises 50, 100, 200, 300, 400, 500, 600, 700, 800, 900, 1000, 2500, 5000, 7500, 10,000 or more unique phase-shift regions. In some embodiments, the sequence of the universal region is substantially the same for each nucleic acid barcode sequence in the library. The phase-shift barcode oligonucleotide sequences can also include a unique molecular identifier, and optionally, a capture region. In some embodiments, a phase-shift barcode oligonucleotide has a length of at least 50, at least 60, at least 70, at least 80, at least 90, at least 100, at least 125, at least 150 nucleotides or more.

In some embodiments, a library of phase-shift barcode oligonucleotides comprises 50, 100, 200, 300, 400, 500, 600, 700, 800, 900, 1000, 2500, 5000, 7500, 10,000, 15,000, 20,000, 30,000, 50,000, 75,000, 100,000, 250,000, 500,000, 1,000,000 or more unique oligonucleotide sequences. In some embodiments, each of the oligonucleotides in a library comprises an oligonucleotide sequence that is unique as compared to other oligonucleotides in the library. In some embodiments, in which a plurality of phase-shift barcode oligonucleotides are present in each partition or on each particle, most or all of the plurality of oligonucleotides within a specific partition or attached to a specific particle are identical to each other, but are unique as compared to phase-shift barcode oligonucleotides that are present in other partitions or are attached to other particles. For instance, each oligonucleotide in a first partition or attached to a first particle may have a different sequence from oligonucleotides in other partitions or attached to other beads, such that at least one nucleotide is different or there is less than 100% sequence identity (e.g., 99%, 95%, 90%, 85%, 80%, 75%, 70%, 65%, 60%, 55%, 50%, or less) between the oligonucleotide of the first partition or first particle and the oligonucleotides of other partitions or particles.

Variable (Barcode) Region

In one aspect, the phase-shift barcode oligonucleotides provided herein comprise one or more variable regions comprising a nucleic acid barcode sequence (or "barcode region"). In some embodiments, the phase-shift barcode oligonucleotide comprises at least one barcode region. The barcode region can be a partition-specific barcode, a molecular barcode, a particle barcode or a combination thereof. The barcode region can contain at least 3 nucleotides, at least 9 nucleotides, 10 nucleotides, 15 nucleotides, or more nucleotides. In some embodiments, the variable or barcode region comprises a random or variable sequence of 6-20 random nucleotides, e.g., 6, 7, 8, 9, 10, 11, 12, 13, 14, 15, 16, 17, 18, 19, or 20 random nucleotides. In some embodiments, the variable or barcode region is about 3-20 nucleotides in length, about 5-15 nucleotides in length, about 6-20 nucleotides in length, about 6-15 nucleotides in length, or about 5-10 nucleotides in length. In some embodiments, each of the plurality of oligonucleotides comprises a variable sequence that is unique from the variable sequences of the other oligonucleotides. In other embodiments, a majority of the variable sequences of the plurality of oligonucleotides are unique sequences.

In some embodiments, the barcode oligonucleotide comprises a partition-specific barcode. In some embodiments, the partition-specific barcode has a length of about 3-200, 3-20, or 16-200 nucleotides. In some embodiments, the partition-specific barcode may be the same in the plurality of oligonucleotides conjugated or linked to a solid support surface. In other cases, the partition-specific barcode is different.

In some instances, the barcode oligonucleotide comprises a molecular barcode. In some embodiments, the molecular barcode has a length of about 3-200, 3-20, or 16-200 nucleotides. The molecular barcode may be unique in the plurality of oligonucleotides conjugated or linked to a solid support surface. In some cases, the molecular barcode is different for each species of the plurality.

In some instances, the barcode oligonucleotide comprises a particle barcode. In some embodiments, the particle barcode has a length of about 3-200, 3-20, or 16-200 nucleotides. In some embodiments, the particle barcode is unique in the plurality of oligonucleotides conjugated or linked to a solid support surface.

In some cases, the phase-shift barcode oligonucleotides comprises more than one variable or barcode region. In some embodiments, each variable region comprises 6-20 random nucleotides, e.g., 6, 7, 8, 9, 10, 11, 12, 13, 14, 15, 16, 17, 18, 19, or 20 random nucleotides. In some embodiments, the oligonucleotide comprises 2, 3, 4, 5, 6, 7, 8, 9, 10 or more variable regions. In some embodiments, wherein two or more variable regions are present, the variable regions are separated by one or more universal regions.

In some embodiments, a library of phase-shift barcode oligonucleotides comprises 100, 200, 300, 400, 500, 600, 700, 800, 900, 1000, 2500, 5000, 7500, 10,000, 15,000, 20,000, 30,000, 50,000, 75,000, 100,000, 250,000, 500,000 or more unique barcode sequences or combinations of barcode regions (or "barcode blocks").

Universal Region

The phase-shift barcode oligonucleotides further comprise one or more universal regions. In some embodiments, the universal region or universal regions comprise one or more hybridization or priming sites that is used in a downstream nucleic acid analysis method (e.g., for a ligation, hybridization, or PCR reaction in a sequencing method). In some embodiments, the universal region or universal regions function as a spacer or linker when two or more variable (barcode regions) are present. The universal region can include a defined sequence of at least 6 nucleotides, e.g., 6, 7, 8, 9, 10 or more nucleotides. The universal region can include a defined sequence of 6-100 nucleotides, e.g., 6, 10, 15, 20, 25, 30, 35, 40, 45, 50, 55, 60, 65, 70, 75, 80 85, 90, 95 or 100 nucleotides. In other cases, the phase-shift barcode oligonucleotide comprises more than one universal region, wherein each universal region comprises a defined sequence of 6-100 nucleotides, e.g., 6, 10, 15, 20, 25, 30, 35, 40, 45, 50, 55, 60, 65, 70, 75, 80 85, 90, 95 or 100 nucleotides. In some embodiments, the plurality of oligonucleotides comprises all or substantially all the same defined sequence. In other embodiments, a majority of the defined sequences of the plurality of oligonucleotides are identical.

Phase-Shift Region

In some embodiments, the barcode oligonucleotide comprises a phase-shift region. The phase-shift region can be 1-50 nucleotides, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In other embodiments, the phase-shift region has a length of more than 5 nucleotides, more than 7 nucleotides, more than 10 nucleotides, more than 20 nucleotides, more than 30 nucleotides, more than 40 nucleotides, or 50 nucleotides. In some embodiments, the phase-shift region has a length of at least 10 nucleotides. In some embodiments, the phase-shift region has a length of 10-50 nucleotides, 10-40 nucleotides, 10-30 nucleotides, 8-35 nucleotides, 8-20 nucleotides, 15-50 nucleotides, or 15-35 nucleotides. The sequence and length of the phase-shift region is selected such that when multiple phase-shift barcode oligonucleotides are aligned with each other, the same nucleotide is not located at the same position of the downstream sequence for all of the oligonucleotides. For instance, for 100 phase-shift barcode oligonucleotides within a library, there may be at least two, e.g., 2, 3, or 4 different nucleotides located at a position of the oligonucleotide downstream of the phase-shift region. In some embodiments, the barcode oligonucleotide does not have more than one phase-shift region.

Phase-shift barcode oligonucleotides disclosed herein are designed to yield at least 2, 3 or 4 different nucleotides at the same position of a universal or defined region of the oligonucleotide sequence when comparing across the oligonucleotides of the library. For instance, a first phase-shift barcode oligonucleotide having a phase-shift region of a first length can have an "A" base at position 10 of the defined region, and a second phase-shift barcode oligonucleotide having a phase-shift region of a second length that is not the same as the first phase-shift region length can have a "G" base at position 10 of the defined region. If such barcode oligonucleotides did not contain a phase-shift region, both oligonucleotides can have the same base at, for example, position 10 of the defined region.

The barcode oligonucleotides of the library can have a phase-shift region of the same length or a different length as another barcode oligonucleotide of the library, so long as within the library all of the barcode oligonucleotides do not have phase-shift regions of the same length. As an example, a first phase-shift region can be 1 nucleotide long, and a second phase-shift region can be 4 nucleotides long. In another example, a first phase-shift region and a second phase-shift region can be 4 nucleotides in length. Phase-shift regions across the plurality of barcode oligonucleotides can have unique or different sequences. For example, at position 1 of a first phase-shift region and a second phase-shift region, there can be two different nucleotides. In some cases, a first and second phase-shift region can have the same nucleotide at a position. Across the library of barcode oligonucleotides, there are least 2, 3, or 4 different nucleotides at each position of the phase-shift region.

Additional Components

In some embodiments, the barcode oligonucleotide comprises a unique molecular identifier (UMI). The UMI sequence of each nucleic acid sequence can be unique among the plurality of sequences. The UMI sequence can be 6-20 nucleotides, e.g., 6, 7, 8, 9, 10, 11, 12, 13, 14, 15, 16, 17, 18, 19 or 20 nucleotides in length.

In some embodiments, each of the barcode oligonucleotides comprises a capture region. The capture region may be located at the 3' end of the sequence. The capture region can include a random nucleotide sequence (e.g., randomer sequence), a poly-thymine (poly(T)) nucleotide sequence, or a poly-adenosine (poly(A)) nucleotide sequence. In some embodiments, the capture region is at least 10 nucleotides in length, at least 25 nucleotides in length, at least 35 nucleotides in length, at least 50 nucleotides in length, at least 75 nucleotides in length, at least 100 nucleotides in length, or longer. In some embodiments, the capture region has a length of about 10-100 nucleotides, about 10-75 nucleotides, about 10-50 nucleotides, about 10-25 nucleotides, or about 20-50 nucleotides. In some embodiments, the capture region comprises a poly-thymine sequence or a poly-adenosine sequence. The sequence of the capture region can include 10-25, 15-30, or 20-45 contiguous thymine residues, or more. Alternatively, the sequence of the capture region can include 10-25, 15-30, or 20-45 contiguous adenosine residues, or more. Optionally, the random nucleotide sequence can be a random pentamer, hexamer, septamer, or octamer. In some cases, the capture region comprises a nucleotide sequence comprising a portion of a sequence of a target nucleic acid or the reverse complement thereof.

The capture region can be any sequence capable of capturing (or hybridizing to) a target nucleic acid or a plurality of target nucleic acids. For example, the capture region can be a poly-thymine nucleotide sequence (e.g., 10-25 or more contiguous thymine nucleotides). As another example, the reverse complement of the capture region can hybridize to a conserved region of a gene family.

In some embodiments, the barcode oligonucleotides comprises an adapter region. In some embodiments, the adapter is used for specific next-generation sequencing platforms. For example, P5 and P7 adapter sequences are known in the art for use with Illumina sequencing chemistry. See, e.g., Bentley et al., *Nature*, 2008, 456:53-59; see also, U.S. Pat. No. 8,192,930. Other adapter sequences are described and are commercially available for other platforms such as those from Pacific Biosciences, Roche, or Ion Torrent™ (Applied Biosciences). In some embodiments, the adapter sequence is about 10-100, about 15-75, about 20-50, or about 10-30 nucleotides in length. The adapter region can be a sequence that is substantially the same or the same for each species of the sequencing library of nucleic acids (e.g., each cDNA of the sequencing library). In some cases, the nucleic acid (e.g., cDNA) can be amplified using a primer that can hybridize to the adapter sequence or a reverse complement thereof.

2. Particles

In some embodiments, the phase-shift barcode oligonucleotides are attached to a particle or bead. In some embodiments, the particle or bead of the present invention can be any particle or bead having a solid support surface. Solid supports suitable for particles include controlled pore glass (CPG)(available from Glen Research, Sterling, Va.), oxalyl-controlled pore glass (See, e.g., Alul, et al., Nucleic Acids Research 1991, 19, 1527), TentaGel Support—an aminopolyethyleneglycol derivatized support (See, e.g., Wright, et al., Tetrahedron Letters 1993, 34, 3373), polystyrene, Poros (a copolymer of polystyrene/divinylbenzene), or reversibly cross-linked acrylamide. Many other solid supports are commercially available and amenable to the present invention. In some embodiments, the bead material is a polystyrene resin or poly(methyl methacrylate) (PMMA). The bead material can be metal.

In some embodiments, the particle or bead comprises hydrogel or another similar composition. In some cases, the hydrogel is in sol form. In some cases, the hydrogel is in gel form. An exemplary hydrogel is an agarose hydrogel. Other hydrogels include, but are not limited to, those described in, e.g., U.S. Pat. Nos. 4,438,258; 6,534,083; 8,008,476; 8,329, 763; U.S. Patent Appl. Nos. 20020009591; 20130022569; 20130034592; and International Patent Publication Nos. WO1997030092; and WO2001049240. Additional compositions and methods for making and using hydrogels, such as barcoded hydrogels, include those described in, e.g., Klein et al., *Cell*, 2015 May 21; 161(5):1187-201.

The solid support surface of the bead can be modified to include a linker for attaching barcode oligonucleotides. The linkers may comprise a cleavable moiety. Non-limiting examples of cleavable moieties include a disulfide bond, a dioxyuridine moiety, and a restriction enzyme recognition site.

In some embodiments, the oligonucleotide conjugated to the particle (e.g., a linker) comprises a universal oligonucleotide (universal region) that is directly attached, conjugated, or linked to the solid support surface. In some embodiments, the universal oligonucleotide that is attached to a bead is used for synthesizing a phase-shift barcode oligonucleotide onto the bead. See, e.g., FIG. 4. The universal oligonucleotide of the plurality of the oligonucleotides can be all or substantially all the same. Each universal region attached to a particle or bead may have the same sequence. The universal oligonucleotide can be configured to covalently link to the solid support surface. In some cases, the oligonucleotide is covalently linked to the hydrogel of the particle. Numerous methods for covalently linking an oligonucleotide to one or more hydrogel matrices are known in the art. For instance, aldehyde derivatized agarose can be covalently linked to a 5'-amine group of a synthetic oligonucleotide.

In some embodiments, the universal oligonucleotide is conjugated to a high molecular weight (e.g., at least about 5, 10, 15, 20, 25, 30, 35, 40, 50 kDa, or more) polymer that can be sterically constrained within a gel form hydrogel matrix. For example, the oligonucleotide can be conjugated to a high molecular weight linear or branched polyacrylamide. As another example, the oligonucleotide can be conjugated to a high molecular weight nucleic acid. The high molecular weight polymer oligonucleotide conjugate (e.g., linear polyacrylamide oligonucleotide conjugate) can be incorporated into a hydrogel matrix by mixing with sol hydrogel and hardening the hydrogel into gel form. Other high molecular weight polymers are suitable for conjugation with an oligonucleotide and encapsulation into a hydrogel. Exemplary polymers include, but are not limited to, dextrans, chitosan, styrenated gelatin, hyaluronic acid, alginate, gelatin, polyethylene glycols, and derivatives thereof.

In some cases, the universal oligonucleotide is conjugated into a linear polyacrylamide by forming a reaction mixture containing one or more acrydite-oligonucleotides and a plurality of acrylamide monomers and polymerizing the reaction mixture to generate a linear polyacrylamide-oligonucleotide conjugate. The reaction can be performed to generate a plurality of linear polyacrylamide-oligonucleotide conjugates. The mean number of oligonucleotides incorporated into the linear polyacrylamide molecules can be controlled by altering the reaction conditions. For example the following non-limiting reaction conditions can be altered to control the average number of incorporated oligonucleotides: pH; temperature; incident light intensity; time of the polymerization reaction; or concentration of oligonucleotide, acrylamide monomer, catalyst (e.g., TEMED), or initiator (e.g., riboflavin or ammonium persulfate).

In one aspect, the present invention provides a library (set or plurality) of particles or beads as described herein. In some embodiments, the library comprises at least 100; 200; 300; 500; 750; 1000; 2000; 3000; 4000; 5000; 6000; 7000; 8000; 9000; 10,000; 20,000; 30,000; 40,000; 50,000; 60,000; 70,000; 80,000; 90,000; 100,000; 250,000; 500,000; 750,000; $1 \times 10^6$; $1 \times 10^7$ or more particles or beads.

B. Methods for Synthesizing Phase-Shifting Barcode Oligonucleotides

For synthesizing barcode oligonucleotides or particles or beads conjugated to barcode oligonucleotides, in some embodiments a universal oligonucleotide (e.g., a universal oligonucleotide such as described above linked to a particle or bead) is used as a primer or base onto which a phase-shift region and one or more barcode regions are added. In some embodiments, a primer binding site is located at the 3' end of the universal oligonucleotide. In some embodiments, the phase-shift region and barcode region or regions are added 3' of the primer binding site. The barcode oligonucleotide can also be synthesized to contain nucleotide sequences of a particle barcode, molecular barcode, partition-specific barcode, defined region, capture region, adapter region, or any combination thereof.

In some embodiments, the barcode oligonucleotides are synthesized using primer extension with template oligonucleotides that hybridize to universal oligonucleotides (also referred to herein as "primer oligonucleotides") or a portion thereof (e.g., the universal region or the primer binding site) and a polymerase. In some instances, the template oligonucleotides comprise a nucleotide sequence containing a partition-specific barcode, molecular barcode, particle barcode, defined region, variable region, phase-shift region, capture region, adapter sequence, and any combination thereof, or reverse complements thereof. In some embodiments, the template oligonucleotide comprises a universal region, a variable region, and a phase-shift region and further comprises a sequence that is complementary to a portion of the primer oligonucleotide sequence. In some embodiments, the template oligonucleotide comprises a capture region. In some embodiments, the template oligonucleotide comprises a unique molecular identifier sequence. In some embodiments, the template oligonucleotide comprises an adapter region. In some embodiments, the template oligonucleotide comprises a sequence that can bind or hybridize to a portion of the nascent barcode oligonucleotide that is being synthesized.

For introducing phase-shifted barcode oligonucleotides by primer extension, a first round of primer extension is conducted using a plurality of different template oligonucleotides, wherein the template oligonucleotides comprise a phase-shift region and wherein the phase-shift regions of the template oligonucleotides are not all of the same length. In some embodiments, a plurality of template oligonucleotides are used, wherein there are at least 2, 3, 4, 5, 6, 7, 8, 9, 10, 20, 30, 40, 50, 60, 70, 80, 90, 100 or more unique phase-shift regions in the set of template oligonucleotides. In some embodiments, the plurality of template oligonucleotides comprises phase-shift regions of variable length and variable nucleotide composition.

In some embodiments, a round of primer extension comprises hybridizing or annealing a template oligonucleotide to at least a portion of the primer oligonucleotide (e.g., to a universal region, a primer binding site and/or an adapter region) or nascent barcode oligonucleotide, and extending the primer oligonucleotide or nascent barcode oligonucleotide (e.g., a primer oligonucleotide or nascent barcode oligonucleotide conjugated to a bead) using a polymerase. After primer extension, the template oligonucleotides can be displaced from the nascent barcode oligonucleotide. The barcode oligonucleotides (e.g., barcode beads) may be split into a plurality of partitions. In some embodiments, the barcode oligonucleotide is synthesized in multiple rounds (e.g., at least two rounds) of primer extension. A different template oligonucleotide for annealing to the primer oligonucleotide or nascent barcode oligonucleotide (e.g., a primer oligonucleotide or nascent barcode oligonucleotide attached to a bead) can be used in each round to further extend the nucleic acid barcode sequence. After each round of extension, the template oligonucleotide is removed or separated from the growing barcode oligonucleotide (e.g., barcode bead). The barcode oligonucleotides (e.g., barcode beads) can be split into a plurality of partitions. Multiple rounds of primer extension can be performed until the entire barcode oligonucleotide is synthesized. In some embodiments, the template oligonucleotides that are used for primer extension for rounds subsequent to the first round of primer extension do not comprise a phase-shift region (i.e., template oligonucleotides comprising a phase-shift region are only used for a first round of primer extension).

The oligonucleotide sequences for use in primer extension can be prepared by a variety of methods including but not limited to cloning of appropriate sequences and direct chemical synthesis using methods well known in the art (Narang et al., *Methods Enzymol.* 68:90 (1979); Brown et al., *Methods Enzymol.* 68:109 (1979)). Oligonucleotides (e.g., template oligonucleotides) can also be obtained from commercial sources such as Integrated DNA Technologies, Operon Technologies, Amersham Pharmacia Biotech, Sigma, or Life Technologies. In some cases, oligonucleotides (e.g., template oligonucleotides) are synthesized using a standard oligonucleotide synthesizer.

Oligonucleotides (e.g., template oligonucleotides) described herein can be synthesized using standard methods known to those in the art. The oligonucleotides can be synthesized from 3' to 5' or from 5' to 3'. Methods of synthesizing can include conversion to the phosphoramidite followed by solid phase chemistries. Representative solid phase techniques are those typically employed for DNA and RNA synthesis using standard phosphoramidite chemistry (see, e.g., Protocols for Oligonucltides and Analogs, Agrawal, S., ed., Humana Press, Totowa, N.J., 1993).

The polymerase can be a DNA polymerase. The polymerase can be a Klenow Fragment, such as a Klenow Fragment (3'→5'exo-polymerase). The DNA polymerase can comprise 3' to 5' exonuclease activity. The DNA polymerase can comprise 5' to 3' exonuclease activity. The DNA polymerase can comprise both 3' to 5' exonuclease activity and 5' to 3' exonuclease activity. The DNA polymerase can comprise neither 3' to 5' exonuclease activity nor 5' to 3' exonuclease activity. The DNA polymerase can comprise strand displacement activity. In some cases, the DNA polymerase does not comprise strand displacement activity.

Barcode oligonucleotides (e.g., barcode oligonucleotides attached to particles) can be synthesized using a split, conjugate, and mix method. In some embodiments, the method is performed by providing a plurality of oligonucleotides (e.g., oligonucleotides attached to particles or beads) for performing solid phase oligonucleotide synthesis. In some cases the particles are provided with one or more oligonucleotides conjugated thereon.

In some embodiments, the barcode oligonucleotides or barcode particles can be split into multiple reaction mixtures, e.g., four different reaction mixtures, each reaction mixture conjugated to a different nucleotide to the particles. For instance, a first reaction mixture conjugates adenine, a second reaction mixture conjugates cytosine, a third reaction mixture conjugates guanine, and a fourth reaction mixture conjugates thymine. In other embodiments, 98-384 different reaction mixtures are used. In some cases, each reaction mixture conjugates a different oligonucleotide. After conjugation is completed, the products of the different reaction mixture are then combined, mixed and split into multiple reaction mixtures. For example, the products can be split into four different reaction mixtures, each reaction mixture conjugating a different nucleotide to the particles. As another example, the products can be split into 98-384 different reaction mixtures, each reaction mixture can conjugate a different oligonucleotide. The splitting, conjugating, and mixing can be repeated to produce a unique barcode for each particle.

In some embodiments, the number of repeats is selected so the number of possible particle barcode sequences exceeds the number of particles or beads by at least 2-fold, 10-fold, 100-fold or more. Splitting, conjugating, and mixing can be repeated from about 1 to about 50 times, from about 2 to about 20 times, from about 5 to about 20 times, about 5 to about 50 times, about 10 to about 20 times, about 10 to about 50 times or more. In some cases, splitting, conjugating, and mixing can be repeated from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more times.

C. Methods for Analyzing Nucleic Acid from Cells

Provided herein are methods for analyzing nucleic acid. In some embodiments, the method comprises analyzing nucleic acid from a population of cells. In some embodiments, a plurality of nucleic acid barcode beads and a population of cells are provided and partitioned. In some embodiments, a unique nucleic acid barcode sequence bead is found in each partition of a plurality. The method described herein can be performed such that at least 90%, 95%, 99% or more of the partitions each contain a single unique nucleic acid barcode sequence. For instance, each partition can contain one or millions of copies or more of a single unique barcode sequence. In some cases, a first partition contains a different nucleic acid barcode sequence than a second partition.

In some cases, each partition includes a single bead and a single cell. In other cases, each partition includes a single bead and target nucleic acid from a single cell. In some embodiments, the partitions on average have about 1 bead and about 1 cell. The target nucleic acid can be produced by lysing the population of cells before or after partitioning. Cells can be lysed by methods commonly known in the art. Exemplary methods for lysing cells include heating the partitions or incorporating detergent into the partitions.

The capture region of the nucleic acid barcode bead can be configured to hybridize to one or more target nucleic acids, e.g., RNA. As such, a complex can form between the barcode sequence and a target nucleic acid.

The target nucleic acid in each partition can be barcoded by performing template directed nucleic acid polymerization in the partition, wherein the polymerization is primed by the capture region of the nucleic acid barcode bead. For example, the capture region hybridize to target nucleic acid(s) in the cell, and the polymerization occurs. In some cases, the capture region comprises a poly-thymine sequence and hybridizes to mRNA of the cell. In such cases, polymerization can comprise reverse transcription. Additionally, or in the alternative, polymerization can comprise amplification of RNA, mRNA, microRNA, DNA, or cDNA.

Partitions can contain template directed nucleic acid polymerization reagents. Non-limiting examples of template directed nucleic acid polymerization reagents include polymerases (e.g., thermostable DNA polymerase, or reverse transcriptase), nucleotides, buffers, salts, oligonucleotide primers, labels, etc. Template directed nucleic acid polymerization reagents further include reagents for performing reverse transcription.

Polymerization primed by the capture region of the barcode sequence can barcode the target nucleic acid of the cell or polymerization products thereof (e.g., amplicons, cDNA, etc.). The resulting barcoded nucleic acid can contain a barcode that uniquely identifies the single cell from which it derives. In some cases, the barcoded nucleic acid contains a molecular barcode that uniquely identifies the nucleic acid molecule from which it derives. A molecular barcode can comprise a nucleotide sequence that is unique to each barcode oligonucleotide. After the nucleic acid is barcoded, the nucleic acid can be recovered from the partition or set of partitions for downstream processing. Sequencing (e.g., high throughput sequencing) can be performed on the barcoded nucleic acids.

In some embodiments, the barcoded nucleic acids are fragmented to obtain nucleic acid products of a desired size or size distribution. Methods of fragmentation are known in the art and include physical methods such as sonication or shearing, chemical methods, and enzymatic methods (e.g., DNase I).

Fragmented barcoded nucleic acid can be hybridized to one or more additional primers to add adapter sequences and amplified. In some cases, the fragmented barcoded nucleic acids are contacted with a terminal transferase to add a polynucleotide (e.g., poly-A, poly-T, poly-G, or poly-C) to generate one or more adapter primer binding sites. Alternatively, the fragmented barcoded nucleic acid can be ligated to one or more adapter oligonucleotides. The adapters can contain sequencing primer binding sites and other sequences useful for quantitation and/or high throughput sequencing.

Adapters can comprise single stranded nucleic acid or double stranded nucleic acid. Adapters can contain a primer binding site, probe binding site or oligonucleotide hybridization site. Such sites can be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more bases. Adapter can also comprise one or more restriction enzyme binding sites. In some embodiments, the adapter includes a modification such as a detectable moiety, a modified base, and the like.

The barcoded nucleic acids can be amplified. In some embodiments, amplification is performed after first strand synthesis, after second strand synthesis, and/or after adapter addition. Methods for DNA amplification include but are not limited to polymerase chain reaction (PCR), ligase chain reaction (LCR), a transcription-based amplification system (TAS), nucleic acid sequence-based amplification (NASBA), strand displacement amplification (SDA), rolling circle amplification (RCA), hyper-branched RCA (HRCA), and the like. Additional examples of amplification methods are found in U.S. Patent Appl. Publ. No. 20150011432, the disclosure is herein incorporated by reference in its entirety for all purposes.

Exemplary high throughput sequencing methods include pyrosequencing, sequencing-by-ligation, single molecule sequencing, sequence-by-synthesis (SBS), massive parallel clonal, massive parallel single molecule SBS, massive parallel single molecule real-time sequencing, massive parallel single molecule real-time nanopore technology, fluorescence-based sequencing, etc. Morozova and Marra provide a review of some such technologies in *Genomics*, 92: 255 (2008), herein incorporated by reference in its entirety. Such sequencing methods, reagents, and platforms are commercialized by VisiGen, Oxford Nanopore Technologies Ltd., Life Technologies, Pacific Biosciences, Roche, Helicos BioSciences, Stratos Genomics, Illumina, and the like. Non-limiting examples of next-generation sequencing methods are found in U.S. Patent Appl. Publ. No. 2015/0011432, the disclosure is herein incorporated by reference in its entirety for all purposes.

D. Kits

Kits are provided analyzing nucleic acids of a cell. In some embodiments, a kit comprises a plurality (library) of phase-shift barcode oligonucleotides as described herein. In some embodiments, a kit comprises a plurality (library) of synthesized barcode oligonucleotide beads as described herein. In some embodiments, the kit also contains reagents for partitioning the beads into a plurality of partitions. The reagent can include a water immiscible liquid. The liquid can be used to form emulsion droplets. In some cases, the reagents include an apparatus containing a plurality of microchannels, or a plurality of microwells or nanowells. Optionally, the kit can contain an instruction manual.

IV. Examples

The following examples are offered to illustrate, but not to limit, the claimed invention.

Example 1. Advantages of Phase-Shift Barcode Oligonucleotides

This example illustrates how incorporating a phasing-shift sequence into a barcode oligonucleotide is a cost- and time-effective method of generating a large diversity of barcodes.

Typically in massive parallel sequencing methods, a large number of barcodes are needed for distinguishing sequences. For generating a large number of barcodes, several shorter barcode regions (or "blocks") may be combined to form larger barcode sequences. For instance, there may be 100 unique barcodes in block 1, 100 unique barcodes in block 2, and 100 unique barcodes in block 3, which when the three blocks are combined yields 1,000,000 combinations or "full" barcodes. To link the blocks together, a constant region that includes a constant priming site is needed as well. Typically, 4-5 constant regions are used to link three different blocks. See, e.g., FIG. 1.

However, this barcode construction method can lead to problems during the sequencing of the sequences. The barcode oligonucleotides can contain regions that are constant or the same for each oligonucleotide. Without the use of phase-shifting regions, the same nucleotide can be found at the same position in all of the barcode oligonucleotides of a sequencing library. For sequencing applications, the presence of the same base at the same position for each barcode can lead to inaccurate base calling, diminished sequence quality, and/or run failures.

FIG. 1 shows a standard method of synthesizing barcode oligonucleotides without the use of phase-shift sequences. The aim is to use a small number of barcode building blocks to create a large number of full-length barcode oligonucleotides. 3 building blocks are illustrated in this example. Each building block contains 9 possible barcodes (BC1-BC9) and a constant region (grey) to link them together, as shown by the groups of sequences SEQ ID NOs:23-31, SEQ ID NOs:32-58, and SEQ ID NOs:59-85. At least 2-3 different constant regions have to be used to avoid low base diversity at each base position. In order to be able to synthesize all possible combinations using these building blocks in this example, 63 (i.e., 9+27+27) oligonucleotides are needed. SEQ ID NO:86 and SEQ ID NO:87 are exemplary barcode oligonucleotides.

FIG. 2 shows the method provided herein used to create barcode oligonucleotides using phase-shift sequences. The aim is to use a small number of barcode building blocks to create a large number of full-length barcode oligonucleotides. 3 building blocks are illustrated in this example. Each building block has 9 possible barcodes and a constant region (grey) to link them together, as shown by the groups of sequences SEQ ID NOs:88-96, SEQ ID NOs:97-105, and SEQ ID NOs:106-114. Since some of the sequences are phase shifted due to the phase-shift blocks (e.g., as shown in SEQ ID NOs:91-96), a single constant region can even be used without causing low diversity at each base position. In order to be able to synthesize all possible combinations using these building blocks in this example, only 27 (i.e., 9+9+9) oligonucleotides are needed. SEQ ID NO:115 and SEQ ID NO:116 are exemplary barcode oligonucleotides.

Taking this example further, in order to synthesize 1,000,000 full-length barcodes using three building blocks, each block has to have 100 distinct barcodes (100×100×100=1,000,000). Using the standard method which utilizes 4 different constant regions as linkers, 900 (i.e., 100+400+400) oligonucleotides as raw building material would be necessary. By using the phase-shift blocks provided herein, the number of oligonucleotides needed decreases to 300 (i.e., 100+100+100). Thus, the phase-shift blocks provide a cost-reducing advantage since fewer oligonucleotides need to be generated or synthesized to create sufficient sequence diversity.

In summary, barcode combinations that contain phase-shift sequences can provide sufficient diversity for sequencing application using a smaller number of building block oligonucleotides than is required for standard methods of synthesizing barcode oligonucleotides from barcode building blocks. Furthermore, when using the phase-shift barcode oligonucleotides, the same nucleotides in the constant regions do not align at the same position for all of the phase-shift barcode oligonucleotides. See, FIG. 3. This feature advantageously prevents or minimizes possible sequencing failures and inaccuracies.

Example 2. Synthesizing Phase-Shift Barcodes on Gel Beads

This example illustrates a method for building barcode oligonucleotides that contain phase-shift nucleotides. The method includes successive rounds of primer extension and splitting to generate a barcode oligonucleotide containing a universal region, primer binding site, defined region, variable region, unique molecular identifier, and capture region.

Figure 3:
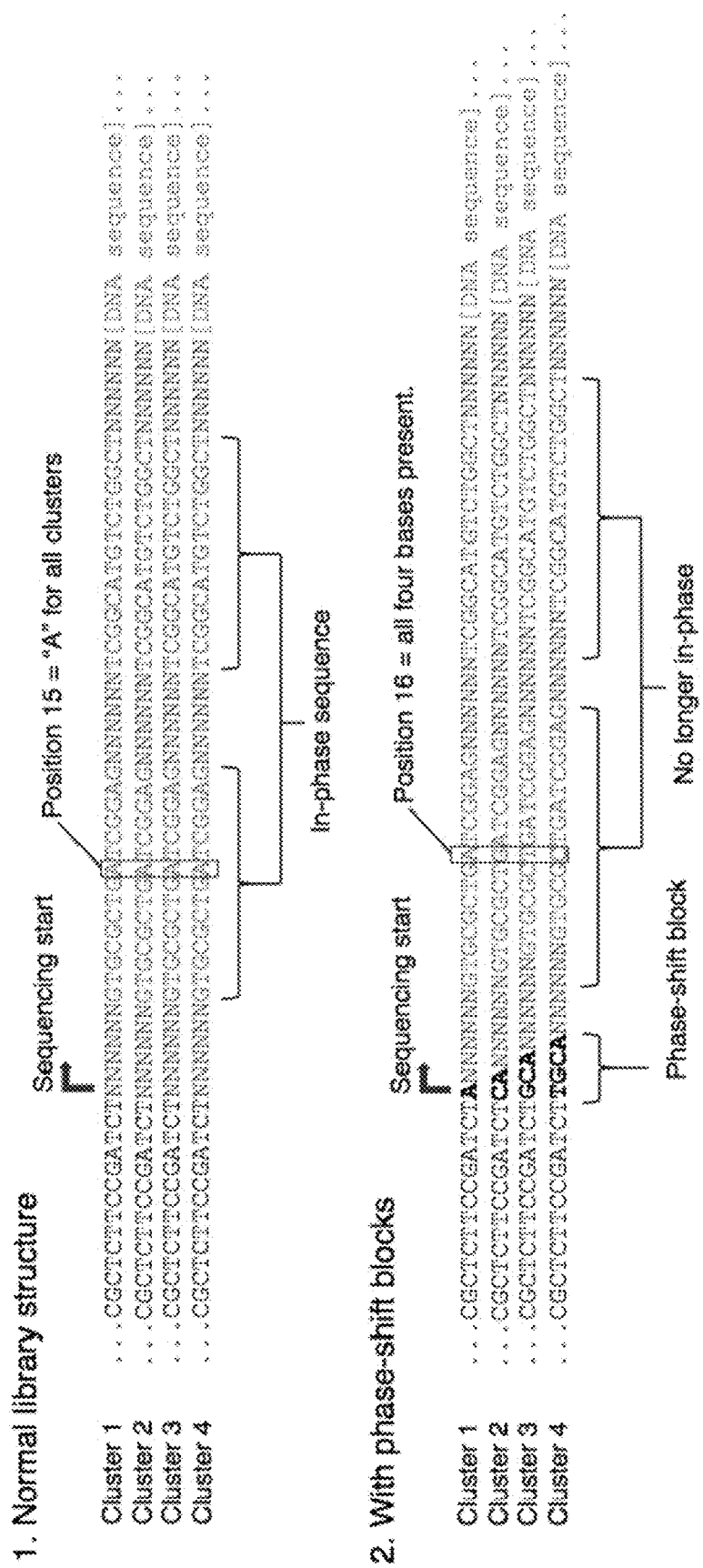
FIG. 3 shows a standard sequencing library (SEQ ID NO:1; top panel) and a phase-shifted sequencing library (SEQ ID NOs:2-5; bottom panel). In the standard library structure, when exemplary DNA clusters 1-4 are aligned, for each position of the constant or defined region the base is the same for all of clusters 1-4. For example, an "A" base is found at position 15 in all of clusters 1-4. Thus, the constant or defined regions of clusters 1-4 are in-phase. In the phase-shifted sequencing library, when exemplary DNA clusters 1-4 are aligned, a different base is found at position 16 in for each of clusters 1-4 (SEQ ID NOS:2-5, respectively). Thus, the constant or defined regions of clusters 1-4 are no longer in-phase.

FIG. 3 shows an exemplary sequence library generated using standard barcode oligonucleotides (SEQ ID NO:1), and an exemplary sequence library generated using phase-shift barcode oligonucleotides (SEQ ID NO:2-5). The sequencing start site of the phase-shift library includes the phase-shift block. Position 16 of the phase-shift sequences in clusters 1-4 contains all four bases that are possible. In contrast, position 15 of the standard sequences in clusters 1-4 contain the same base, e.g., an "A" in all the clusters.

Figure 4:
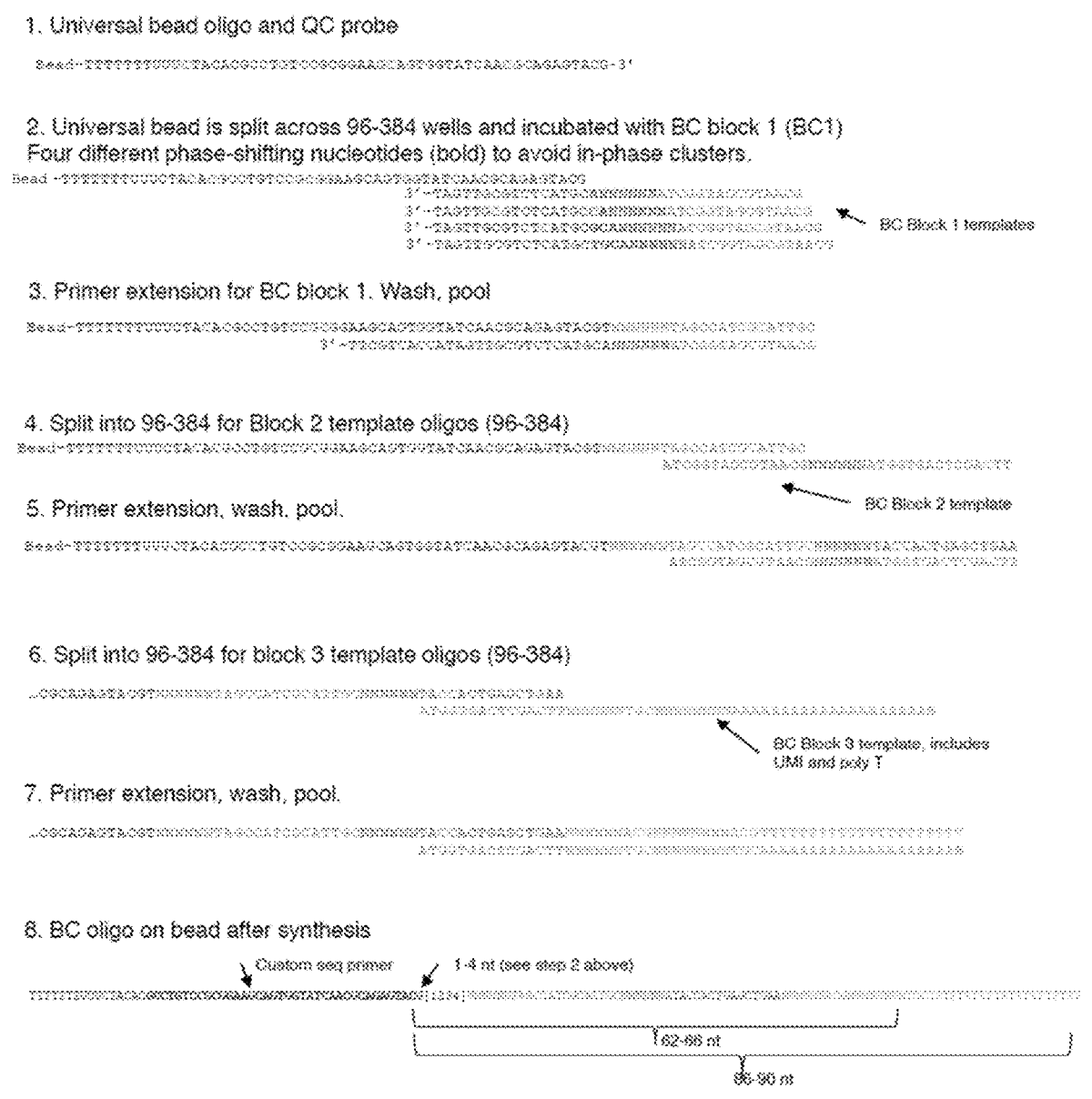

FIG. 4 shows a method for generating the synthetic barcode oligonucleotides on beads as described herein. In step 1, beads are produced that have attached to them a universal bead oligonucleotide (SEQ ID NO:11), or "primer oligonucleotide," that acts as a primer or base for rounds of primer extension. Optionally, the oligonucleotide can include a primer binding site or an adapter sequence (e.g., for a sequencing application). The beads are washed in a buffer such as 1×NEBuffer 2. In step 2, the beads are split into 12 tubes of about 25 µl or across 96-384 wells. The beads are incubated with 1 µl of each of several barcode block 1 template oligonucleotides that each comprise: a sequence that can anneal to at least a portion of the oligonucleotide attached to the bead (e.g., 5'-CGTACTCTGCGTTGAT; SEQ ID NO:6), a phase-shift sequence (e.g., A, CA, GCA, or TGCA), a variable region (e.g., NNNNNN), and a constant region (e.g., 5'-GCAATGCGATGGCTA; SEQ ID NO:7). The exemplary barcode block 1 template oligonucleotides of FIG. 4 are SEQ ID NO:12, SEQ ID NO:13, SEQ ID NO:14, and SEQ ID NO:15. The mixture is heated to 65° C. and cooled at 0.1° C./sec to 19° C. (step 3). In step 4, Klenow (25 µl) buffer and dNTPs for primer extension are added and incubated at 25° C. for 30 minutes. To stop the reaction (step 5), 25 µl of 30 mM EDTA is added and the mixture is heated to 70° C. to inactivate/denature the enzyme. The beads are then pooled together and washed three times with 200 mM NaOH (step 6). The beads are then washed with 1×NEBuffer 2 three times (step 7). To add additional blocks of nucleotide sequence (e.g., additional barcode blocks), steps 2-7 are repeated using the barcode block 2 template oligonucleotide containing a sequence that hybridizes to the nascent barcode oligonucleotide (e.g., 5'-GCAATGCGATGGCTA; SEQ ID NO:7), a variable region (e.g., NNNNNN), and a constant region (e.g., 5'-TTCAGCTCAGTGGTA; SEQ ID NO:8); the exemplary block 2 template oligonucleotide in FIG. 4 is SEQ ID NO:18. The resulting barcode oligonucleotide beads are split into 96-384 wells, and steps 2-7 are repeated with the barcode block 3 template oligonucleotide that contains a sequence that hybridizes to the nascent barcode oligonucleotide (e.g., 5'-TTCAGCTCAGTGGTA; SEQ ID NO:8), a unique molecular identifier (e.g., 5'-NNNNNNCGTNNNNNNNN; SEQ ID NO:9) and a poly (A) sequence (5'-BAAAAAAAAAAAAAAAAAAAA; SEQ ID NO:10); the exemplary block 3 template oligonucleotide in FIG. 4 is SEQ ID NO:20. In the primer extension for the third extension, Klenow 3'→5' exo-polymerase is used at 18° C. Exo+Klenow polymerase is added to edit the poly(A) tail or polish the end of the barcode oligonucleotide that is not attached to the bead.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for analyzing nucleic acid of a population of cells comprising:
   providing:
   (i) a library of barcode oligonucleotides, each barcode oligonucleotide comprising in the 5' to 3' direction, a phase-shift region, a universal region, a variable region, and a capture region, wherein a first nucleotide of the universal region of a first barcode oligonucleotide is staggered by 1 to 50 nucleotides from the first nucleotide of the universal region of a second barcode oligonucleotide; or
   (ii) a library of barcode beads comprising a plurality of beads, wherein each bead is conjugated to a plurality of barcode oligonucleotides and wherein each bead in the library is conjugated to a unique barcode oligonucleotide, each barcode oligonucleotide comprising in the 5' to 3' direction, a phase-shift region, a universal region, a variable region, and a capture region, wherein the first nucleotide of the universal region of a first barcode oligonucleotide is staggered by 1 to 50 nucleotides from the first nucleotide of the universal region of a second barcode oligonucleotide, and wherein for each bead, at least two identical copies of a barcode oligonucleotide is conjugated to the bead;
   providing a population of cells;
   partitioning the library of barcode oligonucleotides or the library of barcode oligonucleotide beads, and the population of cells to generate a plurality of partitions, wherein individual partitions of the plurality have copies of a single barcode oligonucleotide and nucleic acid from a single cell;
   in the partitions lysing the cells to generate nucleic acid from a single cell in individual partitions;
   hybridizing the copies of the barcode oligonucleotide to the nucleic acid from the single cell in the partitions;
   performing template directed nucleic acid polymerization to covalently attach oligonucleotide primers to the nucleic acid of the single cell in the partitions;
   combining the partitions; and
   performing high-throughput sequencing.

2. The method of claim 1, wherein the nucleic acid of the single cell is RNA or cDNA.

3. The method of claim 1, wherein the template directed nucleic acid polymerization comprises reverse transcription.

4. The method of claim 1, wherein the template directed nucleic acid polymerization comprises DNA amplification.

5. The method of claim 1, wherein the providing comprises providing the library of barcode oligonucleotides.

6. The method of claim 5, wherein each barcode oligonucleotide is attached to a bead.

7. The method of claim 5, wherein each barcode oligonucleotide comprises more than one variable region.

8. The method of claim 5, wherein each barcode oligonucleotide comprises more than one universal region.

9. The method of claim 5, wherein the capture region comprises a polyT sequence of at last ten thymine nucleotides.

10. The method of claim 1, wherein the providing comprises providing the library of barcode beads.

11. The method of claim 10, wherein each barcode oligonucleotide comprises more than one variable region.

12. The method of claim 10, wherein each barcode oligonucleotide comprises more than one universal region.

13. The method of claim 10, wherein each barcode oligonucleotide further comprises a unique molecular identifier.

14. The method of claim 10, wherein the capture region comprises a polyT sequence of at last ten thymine nucleotides.

15. The method of claim 10, wherein each bead is conjugated to at least two different barcode oligonucleotides.

16. The method of claim 10, wherein each barcode oligonucleotide comprises an adapter sequence.

* * * * *

SEQUENCE LISTING

<160> NUMBER OF SEQ ID NOS: 118

<210> SEQ ID NO 1

-continued

```
<211> LENGTH: 62
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (15)..(20)
<223> OTHER INFORMATION: n = any nucleotide
<220> FEATURE:
<221> NAME/KEY: misc_feature
<222> LOCATION: (36)..(41)
<223> OTHER INFORMATION: n = any nucleotide
<220> FEATURE:
<221> NAME/KEY: misc_feature
<222> LOCATION: (57)..(62)
<223> OTHER INFORMATION: n = any nucleotide

<400> SEQUENCE: 1
cgctcttccg atctnnnnnn gtgcgctgat cggagnnnnn ntcggcatgt ctggctnnnn    60 nn                                                                  62

<210> SEQ ID NO 2
<211> LENGTH: 63
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide
<220> FEATURE:
<221> NAME/KEY: misc_feature
<222> LOCATION: (37)..(42)
<223> OTHER INFORMATION: n = any nucleotide
<220> FEATURE:
<221> NAME/KEY: misc_feature
<222> LOCATION: (58)..(63)
<223> OTHER INFORMATION: n = any nucleotide

<400> SEQUENCE: 2
cgctcttccg atctannnnn ngtgcgctga tcggagnnnn nntcggcatg tctggctnnn    60 nnn                                                                 63

<210> SEQ ID NO 3
<211> LENGTH: 64
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide
<220> FEATURE:
<221> NAME/KEY: misc_feature
<222> LOCATION: (38)..(43)
<223> OTHER INFORMATION: n = any nucleotide
<220> FEATURE:
<221> NAME/KEY: misc_feature
<222> LOCATION: (59)..(64)
<223> OTHER INFORMATION: n = any nucleotide

<400> SEQUENCE: 3
cgctcttccg atctcannnn nngtgcgctg atcggagnnn nnntcggcat gtctggctnn    60 nnnn                                                                64

<210> SEQ ID NO 4
<211> LENGTH: 65
```

```
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (18)..(23)
<223> OTHER INFORMATION: n = any nucleotide
<220> FEATURE:
<221> NAME/KEY: misc_feature
<222> LOCATION: (39)..(44)
<223> OTHER INFORMATION: n = any nucleotide
<220> FEATURE:
<221> NAME/KEY: misc_feature
<222> LOCATION: (60)..(65)
<223> OTHER INFORMATION: n = any nucleotide

<400> SEQUENCE: 4
cgctcttccg atctgcannn nnngtgcgct gatcggagnn nnnntcggca tgtctggctn    60 nnnnn                                                                65

<210> SEQ ID NO 5
<211> LENGTH: 66
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (19)..(24)
<223> OTHER INFORMATION: n = any nucleotide
<220> FEATURE:
<221> NAME/KEY: misc_feature
<222> LOCATION: (40)..(45)
<223> OTHER INFORMATION: n = any nucleotide
<220> FEATURE:
<221> NAME/KEY: misc_feature
<222> LOCATION: (61)..(66)
<223> OTHER INFORMATION: n = any nucleotide

<400> SEQUENCE: 5
cgctcttccg atcttgcann nnnngtgcgc tgatcggagn nnnnntcggc atgtctggct    60 nnnnnn                                                               66

<210> SEQ ID NO 6
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 6
cgtactctgc gttgat                                                    16

<210> SEQ ID NO 7
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 7
gcaatgcgat ggcta                                                     15

<210> SEQ ID NO 8
<211> LENGTH: 15
<212> TYPE: DNA
<213> ORGANISM: Artificial Sequence
<220> FEATURE:
```

```
<223> OTHER INFORMATION: synthetic oligonucleotide

<400> SEQUENCE: 8
ttcagctcag tggta                                                  15

<210> SEQ ID NO 9
<211> LENGTH: 17
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(6)
<223> OTHER INFORMATION: n = any nucleotide
<220> FEATURE:
<221> NAME/KEY: misc_feature
<222> LOCATION: (10)..(17)
<223> OTHER INFORMATION: n = any nucleotide

<400> SEQUENCE: 9
nnnnnncgtn nnnnnnn                                                17

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 10
baaaaaaaaa aaaaaaaaaa a                                           21

<210> SEQ ID NO 11
<211> LENGTH: 54
<212> TYPE: DNA
<213> ORGANISM: Artificial Sequence
<220> FEATURE:
<223> OTHER INFORMATION: synthetic polynucleotide

<400> SEQUENCE: 11
tttttttuuu ctacacgcct gtccgcggaa gcagtggtat caacgcagag tacg       54

<210> SEQ ID NO 12
<211> LENGTH: 38
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 12
gcaatgcgat ggctannnnn nacgtactct gcgttgat                         38

<210> SEQ ID NO 13
<211> LENGTH: 39
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 13
```

```
gcaatgcgat ggctannnnn naccgtactc tgcgttgat                              39

<210> SEQ ID NO 14
<211> LENGTH: 40
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 14
gcaatgcgat ggctannnnn nacgcgtact ctgcgttgat                             40

<210> SEQ ID NO 15
<211> LENGTH: 41
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 15
gcaatgcgat ggctannnnn nacgtcgtac tctgcgttga t                           41

<210> SEQ ID NO 16
<211> LENGTH: 76
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (56)..(61)
<223> OTHER INFORMATION: n = any nucleotide

<400> SEQUENCE: 16 ttttttttuuu ctacacgcct gtccgcggaa gcagtggtat caacgcagag tacgtnnnnn      60
ntagccatcg cattgc                                                       76

<210> SEQ ID NO 17
<211> LENGTH: 48
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 17
gcaatgcgat ggctannnnn nacgtactct gcgttgatac cactgctt                    48

<210> SEQ ID NO 18
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
```

<223> OTHER INFORMATION: n = any nucleotide

<400> SEQUENCE: 18
ttcagctcag tggtannnnn ngcaatgcga tggcta    36

<210> SEQ ID NO 19
<211> LENGTH: 97
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (56)..(61)
<223> OTHER INFORMATION: n = any nucleotide
<220> FEATURE:
<221> NAME/KEY: misc_feature
<222> LOCATION: (77)..(82)
<223> OTHER INFORMATION: n = any nucleotide

<400> SEQUENCE: 19
tttttttuuu ctacacgcct gtccgcggaa gcagtggtat caacgcagag tacgtnnnnn    60
ntagccatcg cattgcnnnn nntaccactg agctgaa    97

<210> SEQ ID NO 20
<211> LENGTH: 53
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (22)..(29)
<223> OTHER INFORMATION: n = any nucleotide
<220> FEATURE:
<221> NAME/KEY: misc_feature
<222> LOCATION: (33)..(38)
<223> OTHER INFORMATION: n = any nucleotide

<400> SEQUENCE: 20
baaaaaaaaa aaaaaaaaaa annnnnnnnc gtnnnnnntt cagctcagtg gta    53

<210> SEQ ID NO 21
<211> LENGTH: 95
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (13)..(18)
<223> OTHER INFORMATION: n = any nucleotide
<220> FEATURE:
<221> NAME/KEY: misc_feature
<222> LOCATION: (34)..(39)
<223> OTHER INFORMATION: n = any nucleotide
<220> FEATURE:
<221> NAME/KEY: misc_feature
<222> LOCATION: (55)..(60)
<223> OTHER INFORMATION: n = any nucleotide
<220> FEATURE:
<221> NAME/KEY: misc_feature
<222> LOCATION: (64)..(71)
<223> OTHER INFORMATION: n = any nucleotide

<400> SEQUENCE: 21
cgcagagtac gtnnnnnnta gccatcgcat tgcnnnnnnt accactgagc tgaannnnnn    60 acgnnnnnnnn nacgttttttt ttttttttt ttttv    95

```
<210> SEQ ID NO 22
<211> LENGTH: 144
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (55)..(55)
<223> OTHER INFORMATION: n = a
<220> FEATURE:
<221> NAME/KEY: misc_feature
<222> LOCATION: (56)..(56)
<223> OTHER INFORMATION: n = c or absent
<220> FEATURE:
<221> NAME/KEY: misc_feature
<222> LOCATION: (57)..(57)
<223> OTHER INFORMATION: n = g or absent if nucleotide in position 56
      is absent
<220> FEATURE:
<221> NAME/KEY: misc_feature
<222> LOCATION: (58)..(58)
<223> OTHER INFORMATION: n= t or absent if nucleotides in position 56
      and 57 are absent
<220> FEATURE:
<221> NAME/KEY: misc_feature
<222> LOCATION: (60)..(65)
<223> OTHER INFORMATION: n = any nucleotide
<220> FEATURE:
<221> NAME/KEY: misc_feature
<222> LOCATION: (81)..(86)
<223> OTHER INFORMATION: n = any nucleotide
<220> FEATURE:
<221> NAME/KEY: misc_feature
<222> LOCATION: (102)..(109)
<223> OTHER INFORMATION: n = any nucleotide
<220> FEATURE:
<221> NAME/KEY: misc_feature
<222> LOCATION: (113)..(120)
<223> OTHER INFORMATION: n = any nucleotide

<400> SEQUENCE: 22
tttttttuuu ctacacgcct gtccgcggaa gcagtggtat caacgcagag tacgnnnntn      60
nnnnntagcc atcgcattgc nnnnnntacc actgagctga annnnnnnna cgnnnnnnnn     120
tgcaaaaaaa aaaaaaaaaa aaab                                            144

<210> SEQ ID NO 23
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 23
tagttgcgtc tcatgcnnnn nnatcggtag cgtaacg                               37

<210> SEQ ID NO 24
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 24
```
tagttgcgtc tcatgcnnnn nnatcggtag cgtaacg         37

<210> SEQ ID NO 25
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 25
tagttgcgtc tcatgcnnnn nnatcggtag cgtaacg         37

<210> SEQ ID NO 26
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 26
tagttgcgtc tcatgcnnnn nngcatgcgt tactgga         37

<210> SEQ ID NO 27
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 27
tagttgcgtc tcatgcnnnn nngcatgcgt tactgga         37

<210> SEQ ID NO 28
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 28
tagttgcgtc tcatgcnnnn nngcatgcgt tactgga         37

<210> SEQ ID NO 29
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 29
tagttgcgtc tcatgcnnnn nncgtatagc gtagttc   37

<210> SEQ ID NO 30
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 30
tagttgcgtc tcatgcnnnn nncgtatagc gtagttc   37

<210> SEQ ID NO 31
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 31
tagttgcgtc tcatgcnnnn nncgtatagc gtagttc   37

<210> SEQ ID NO 32
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 32
tagccatcgc attgcnnnnn nttactggca ctgatc   36

<210> SEQ ID NO 33
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 33
tagccatcgc attgcnnnnn nttactggca ctgatc   36

<210> SEQ ID NO 34
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

```
<400> SEQUENCE: 34
tagccatcgc attgcnnnnn nttactggca ctgatc                                 36

<210> SEQ ID NO 35
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 35
tagccatcgc attgcnnnnn nttactggca ctgatc                                 36

<210> SEQ ID NO 36
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 36
tagccatcgc attgcnnnnn nttactggca ctgatc                                 36

<210> SEQ ID NO 37
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 37
tagccatcgc attgcnnnnn nttactggca ctgatc                                 36

<210> SEQ ID NO 38
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 38
tagccatcgc attgcnnnnn nttactggca ctgatc                                 36

<210> SEQ ID NO 39
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide
```

<400> SEQUENCE: 39
tagccatcgc attgcnnnnn nttactggca ctgatc         36

<210> SEQ ID NO 40
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 40
tagccatcgc attgcnnnnn nttactggca ctgatc         36

<210> SEQ ID NO 41
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 41
cgtacgcaat gacctnnnnn ngcgcattta tgccat         36

<210> SEQ ID NO 42
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 42
cgtacgcaat gacctnnnnn ngcgcattta tgccat         36

<210> SEQ ID NO 43
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 43
cgtacgcaat gacctnnnnn ngcgcattta tgccat         36

<210> SEQ ID NO 44
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)

<223> OTHER INFORMATION: n = any nucleotide

<400> SEQUENCE: 44
cgtacgcaat gacctnnnnn ngcgcattta tgccat                                    36

<210> SEQ ID NO 45
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 45
cgtacgcaat gacctnnnnn ngcgcattta tgccat                                    36

<210> SEQ ID NO 46
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 46
cgtacgcaat gacctnnnnn ngcgcattta tgccat                                    36

<210> SEQ ID NO 47
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 47
cgtacgcaat gacctnnnnn ngcgcattta tgccat                                    36

<210> SEQ ID NO 48
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 48
cgtacgcaat gacctnnnnn ngcgcattta tgccat                                    36

<210> SEQ ID NO 49
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 49
cgtacgcaat gacctnnnnn ngcgcattta tgccat					36

<210> SEQ ID NO 50
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 50
gcatatcgca tcaagnnnnn ncatggatcg gtcatg					36

<210> SEQ ID NO 51
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 51
gcatatcgca tcaagnnnnn ncatggatcg gtcatg					36

<210> SEQ ID NO 52
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 52
gcatatcgca tcaagnnnnn ncatggatcg gtcatg					36

<210> SEQ ID NO 53
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 53
gcatatcgca tcaagnnnnn ncatggatcg gtcatg					36

<210> SEQ ID NO 54
<211> LENGTH: 36
<212> TYPE: DNA
<213> ORGANISM: Artificial Sequence
<220> FEATURE:
<223> OTHER INFORMATION: synthetic polynucleotide
<220> FEATURE:

```
<221> NAME/KEY: misc_feature
<222> LOCATION: (16)..(21)
<223> OTHER INFORMATION: n = any nucleotide

<400> SEQUENCE: 54
gcatatcgca tcaagnnnnn ncatggatcg gtcatg                              36

<210> SEQ ID NO 55
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 55
gcatatcgca tcaagnnnnn ncatggatcg gtcatg                              36

<210> SEQ ID NO 56
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 56
gcatatcgca tcaagnnnnn ncatggatcg gtcatg                              36

<210> SEQ ID NO 57
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 57
gcatatcgca tcaagnnnnn ncatggatcg gtcatg                              36

<210> SEQ ID NO 58
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 58
gcatatcgca tcaagnnnnn ncatggatcg gtcatg                              36

<210> SEQ ID NO 59
<211> LENGTH: 36
<212> TYPE: DNA
<213> ORGANISM: Artificial Sequence
<220> FEATURE:
<223> OTHER INFORMATION: synthetic polynucleotide
```

```
<220> FEATURE:
<221> NAME/KEY: misc_feature
<222> LOCATION: (16)..(27)
<223> OTHER INFORMATION: n = any nucleotide

<400> SEQUENCE: 59
aatgaccgtg actatnnnnn nnnnnnnttt tttttt                                36

<210> SEQ ID NO 60
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 60
aatgaccgtg actatnnnnn nnnnnnnttt tttttt                                36

<210> SEQ ID NO 61
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 61
aatgaccgtg actatnnnnn nnnnnnnttt tttttt                                36

<210> SEQ ID NO 62
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 62
aatgaccgtg actatnnnnn nnnnnnnttt tttttt                                36

<210> SEQ ID NO 63
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 63
aatgaccgtg actatnnnnn nnnnnnnttt tttttt                                36

<210> SEQ ID NO 64
<211> LENGTH: 36
<212> TYPE: DNA
<213> ORGANISM: Artificial Sequence
<220> FEATURE:
```

```
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 64
aatgaccgtg actatnnnnn nnnnnnnttt tttttt                                  36

<210> SEQ ID NO 65
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 65
aatgaccgtg actatnnnnn nnnnnnnttt tttttt                                  36

<210> SEQ ID NO 66
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 66
aatgaccgtg actatnnnnn nnnnnnnttt tttttt                                  36

<210> SEQ ID NO 67
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 67
aatgaccgtg actatnnnnn nnnnnnnttt tttttt                                  36

<210> SEQ ID NO 68
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 68
cgcgtaaata cggtannnnn nnnnnnnttt tttttt                                  36

<210> SEQ ID NO 69
<211> LENGTH: 36
<212> TYPE: DNA
<213> ORGANISM: Artificial Sequence
```

<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 69
cgcgtaaata cggtannnnn nnnnnntttt tttttt                                    36

<210> SEQ ID NO 70
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 70
cgcgtaaata cggtannnnn nnnnnntttt tttttt                                    36

<210> SEQ ID NO 71
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 71
cgcgtaaata cggtannnnn nnnnnntttt tttttt                                    36

<210> SEQ ID NO 72
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 72
cgcgtaaata cggtannnnn nnnnnntttt tttttt                                    36

<210> SEQ ID NO 73
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 73
cgcgtaaata cggtannnnn nnnnnntttt tttttt                                    36

<210> SEQ ID NO 74
<211> LENGTH: 36
<212> TYPE: DNA

<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 74
cgcgtaaata cggtannnnn nnnnnntttt tttttt         36

<210> SEQ ID NO 75
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 75
cgcgtaaata cggtannnnn nnnnnntttt tttttt         36

<210> SEQ ID NO 76
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 76
cgcgtaaata cggtannnnn nnnnnntttt tttttt         36

<210> SEQ ID NO 77
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 77
gtacctagcc agtacnnnnn nnnnnnnttt tttttt         36

<210> SEQ ID NO 78
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 78
gtacctagcc agtacnnnnn nnnnnnnttt tttttt         36

<210> SEQ ID NO 79
<211> LENGTH: 36

```
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 79
gtacctagcc agtacnnnnn nnnnnnnttt tttttt                              36

<210> SEQ ID NO 80
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 80
gtacctagcc agtacnnnnn nnnnnnnttt tttttt                              36

<210> SEQ ID NO 81
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 81
gtacctagcc agtacnnnnn nnnnnnnttt tttttt                              36

<210> SEQ ID NO 82
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 82
gtacctagcc agtacnnnnn nnnnnnnttt tttttt                              36

<210> SEQ ID NO 83
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 83
gtacctagcc agtacnnnnn nnnnnnnttt tttttt                              36

<210> SEQ ID NO 84
```

```
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 84
gtacctagcc agtacnnnnn nnnnnnnttt tttttt                              36

<210> SEQ ID NO 85
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 85
gtacctagcc agtacnnnnn nnnnnnnttt tttttt                              36

<210> SEQ ID NO 86
<211> LENGTH: 79
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide
<220> FEATURE:
<221> NAME/KEY: misc_feature
<222> LOCATION: (38)..(43)
<223> OTHER INFORMATION: n = any nucleotide
<220> FEATURE:
<221> NAME/KEY: misc_feature
<222> LOCATION: (59)..(70)
<223> OTHER INFORMATION: n = any nucleotide

<400> SEQUENCE: 86
tagttgcgtc tcatgcnnnn nnatcgatag cgtaacgnnn nnnttactgg cactgatcnn    60
nnnnnnnnnn tttttttt                                                  79

<210> SEQ ID NO 87
<211> LENGTH: 79
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide
<220> FEATURE:
<221> NAME/KEY: misc_feature
<222> LOCATION: (38)..(43)
<223> OTHER INFORMATION: n = any nucleotide
<220> FEATURE:
<221> NAME/KEY: misc_feature
<222> LOCATION: (59)..(70)
<223> OTHER INFORMATION: n = any nucleotide

<400> SEQUENCE: 87
tagttgcgtc tcatgcnnnn nnatcgatag cgtaacgnnn nnnttactgg cactgatcnn    60
```
nnnnnnnnnn tttttttt                                                           79

<210> SEQ ID NO 88
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 88
tagttgcgtc tcatgcnnnn nnatcgatag cgtaacg                                      37

<210> SEQ ID NO 89
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 89
tagttgcgtc tcatgcnnnn nnatcgatag cgtaacg                                      37

<210> SEQ ID NO 90
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 90
tagttgcgtc tcatgcnnnn nnatcgatag cgtaacg                                      37

<210> SEQ ID NO 91
<211> LENGTH: 37
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 91
tagttgcgtc tcatgcnnnn nnatcgatag cgtaacg                                      37

<210> SEQ ID NO 92
<211> LENGTH: 38
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 92
tagttgcgtc tcatgcnnnn nngatcgata gcgtaacg					38

<210> SEQ ID NO 93
<211> LENGTH: 38
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 93
tagttgcgtc tcatgcnnnn nngatcgata gcgtaacg					38

<210> SEQ ID NO 94
<211> LENGTH: 39
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 94
tagttgcgtc tcatgcnnnn nngcatcgat agcgtaacg					39

<210> SEQ ID NO 95
<211> LENGTH: 39
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 95
tagttgcgtc tcatgcnnnn nngcatcgat agcgtaacg					39

<210> SEQ ID NO 96
<211> LENGTH: 39
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide

<400> SEQUENCE: 96
tagttgcgtc tcatgcnnnn nngcatcgat agcgtaacg					39

<210> SEQ ID NO 97
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

```
<400> SEQUENCE: 97
tagccatcgc attgcnnnnn nttactggca ctgatc                                 36

<210> SEQ ID NO 98
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 98
tagccatcgc attgcnnnnn nttactggca ctgatc                                 36

<210> SEQ ID NO 99
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 99
tagccatcgc attgcnnnnn nttactggca ctgatc                                 36

<210> SEQ ID NO 100
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 100
tagccatcgc attgcnnnnn nttactggca ctgatc                                 36

<210> SEQ ID NO 101
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 101
tagccatcgc attgcnnnnn nttactggca ctgatc                                 36

<210> SEQ ID NO 102
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
```

<223> OTHER INFORMATION: n = any nucleotide

<400> SEQUENCE: 102
tagccatcgc attgcnnnnn nttactggca ctgatc                              36

<210> SEQ ID NO 103
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 103
tagccatcgc attgcnnnnn nttactggca ctgatc                              36

<210> SEQ ID NO 104
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 104
tagccatcgc attgcnnnnn nttactggca ctgatc                              36

<210> SEQ ID NO 105
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(21)
<223> OTHER INFORMATION: n = any nucleotide

<400> SEQUENCE: 105
tagccatcgc attgcnnnnn nttactggca ctgatc                              36

<210> SEQ ID NO 106
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 106
aatgaccgtg actagnnnnn nnnnnnnttt tttttt                              36

<210> SEQ ID NO 107
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature

```
<222> LOCATION: (16)..(27)
<223> OTHER INFORMATION: n = any nucleotide

<400> SEQUENCE: 107
aatgaccgtg actagnnnnn nnnnnnnttt tttttt                                    36

<210> SEQ ID NO 108
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 108
aatgaccgtg actagnnnnn nnnnnnnttt tttttt                                    36

<210> SEQ ID NO 109
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 109
aatgaccgtg actagnnnnn nnnnnnnttt tttttt                                    36

<210> SEQ ID NO 110
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 110
aatgaccgtg actagnnnnn nnnnnnnttt tttttt                                    36

<210> SEQ ID NO 111
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 111
aatgaccgtg actagnnnnn nnnnnnnttt tttttt                                    36

<210> SEQ ID NO 112
<211> LENGTH: 36
<212> TYPE: DNA
<213> ORGANISM: Artificial Sequence
<220> FEATURE:
<223> OTHER INFORMATION: synthetic polynucleotide
<220> FEATURE:
```

```
<221> NAME/KEY: misc_feature
<222> LOCATION: (16)..(27)
<223> OTHER INFORMATION: n = any nucleotide

<400> SEQUENCE: 112
aatgaccgtg actagnnnnn nnnnnnnttt tttttt                           36

<210> SEQ ID NO 113
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 113
aatgaccgtg actagnnnnn nnnnnnnttt tttttt                           36

<210> SEQ ID NO 114
<211> LENGTH: 36
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (16)..(27)
<223> OTHER INFORMATION: n = any nucleotide

<400> SEQUENCE: 114
aatgaccgtg actagnnnnn nnnnnnnttt tttttt                           36

<210> SEQ ID NO 115
<211> LENGTH: 79
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide
<220> FEATURE:
<221> NAME/KEY: misc_feature
<222> LOCATION: (38)..(43)
<223> OTHER INFORMATION: n = any nucleotide
<220> FEATURE:
<221> NAME/KEY: misc_feature
<222> LOCATION: (59)..(70)
<223> OTHER INFORMATION: n = any nucleotide

<400> SEQUENCE: 115
tagttgcgtc tcatgcnnnn nnatcgatag cgtaacgnnn nnnttactgg cactgatcnn    60
nnnnnnnnnn tttttttt                                                  79

<210> SEQ ID NO 116
<211> LENGTH: 81
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (17)..(22)
<223> OTHER INFORMATION: n = any nucleotide
<220> FEATURE:
<221> NAME/KEY: misc_feature
```

```
<222> LOCATION: (40)..(45)
<223> OTHER INFORMATION: n = any nucleotide
<220> FEATURE:
<221> NAME/KEY: misc_feature
<222> LOCATION: (61)..(72)
<223> OTHER INFORMATION: n = any nucleotide

<400> SEQUENCE: 116
tagttgcgtc tcatgcnnnn nngcatcgat agcgtaacgn nnnnnttact ggcactgatc      60
nnnnnnnnnn nntttttttt t                                                81

<210> SEQ ID NO 117
<211> LENGTH: 54
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (13)..(18)
<223> OTHER INFORMATION: n = any nucleotide
<220> FEATURE:
<221> NAME/KEY: misc_feature
<222> LOCATION: (34)..(39)
<223> OTHER INFORMATION: n = any nucleotide

<400> SEQUENCE: 117
cgcagagtac gtnnnnnnta gccatcgcat tgcnnnnnnt accactgagc tgaa            54

<210> SEQ ID NO 118
<211> LENGTH: 56
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (25)..(32)
<223> OTHER INFORMATION: n = any nucleotide
<220> FEATURE:
<221> NAME/KEY: misc_feature
<222> LOCATION: (36)..(41)
<223> OTHER INFORMATION: n = any nucleotide

<400> SEQUENCE: 118
baaaaaaaaa aaaaaaaaaa acgtnnnnnn nncgtnnnnn nttcagctca gtggta          56
```